United States Patent
Van Wezel et al.

(10) Patent No.: US 9,617,592 B2
(45) Date of Patent: Apr. 11, 2017

(54) SCREENING METHOD FOR MICRO-ORGANISMS AND METHODS FOR THE PRODUCTION OF A PRODUCT

(71) Applicant: Universiteit Leiden, Leiden (NL)

(72) Inventors: Gilles Philippus Van Wezel, Leiden (NL); Jacob Gubbens, Leiden (NL); Hua Zhu, Leiden (NL)

(73) Assignee: Universiteit Leiden, Leiden (NL)

( * ) Notice: Subject to any disclaimer, the term of this patent is extended or adjusted under 35 U.S.C. 154(b) by 0 days.

(21) Appl. No.: 14/403,537

(22) PCT Filed: May 24, 2013

(86) PCT No.: PCT/NL2013/050381
§ 371 (c)(1),
(2) Date: Nov. 24, 2014

(87) PCT Pub. No.: WO2013/176550
PCT Pub. Date: Nov. 28, 2013

(65) Prior Publication Data
US 2015/0152493 A1 Jun. 4, 2015

(30) Foreign Application Priority Data

May 24, 2012 (EP) .................................. 12169178

(51) Int. Cl.
*G01N 33/68* (2006.01)
*C12Q 1/68* (2006.01)
*C12Q 1/02* (2006.01)

(52) U.S. Cl.
CPC ............. *C12Q 1/6869* (2013.01); *C12Q 1/02* (2013.01); *G01N 33/6818* (2013.01); *G01N 33/6851* (2013.01); *G01N 2333/36* (2013.01)

(58) Field of Classification Search
None
See application file for complete search history.

(56) References Cited

FOREIGN PATENT DOCUMENTS

WO 2013176550 A1 11/2013

OTHER PUBLICATIONS

Koskenniemi et al., Proteome analysis of Lactobacillus rhamnosus GG using 2-D DIGE and mass spectrometry shows differential protein production in laboratory and industrial-type growth media, Journal of Proteome Research, Nov. 6, 2009, pp. 4993-5007, vol. 8, No. 11, American Chemical Society, Washington, DC, US.

Hammami et al., Proteomic analysis of the metabolic adaptation of the biocontrol agent Pseudozyma flocculosa leading to glycolipid production, Proteome Science, Feb. 9, 2010, p. 7, vol. 8, No. 1, Biomed Central, London, GB.

Bruns et al., Functional genomic profiling of Aspergillus fumigatus biofilm reveals enhanced production of the mycotoxin gliotoxin, Proteomics, Sep. 1, 2010, pp. 3097-3107, vol. 10, No. 17.

Kim et al., Acidic pH shock induces the expressions of a wide range of stress-response genes, BMC Genomics, Dec. 16, 2008, p. 604, vol. 9, No. 1, Biomed Central Ltd., London, UK.

Oldham et al., Shotgun proteomic analysis of yeast-elicited California poppy (Eschscholzia californica) suspension cultures producing enhanced levels of benzophenanthridine alkaloids, Journal of Proteome Research, Sep. 3, 2010, pp. 4337-4345, vol. 9, No. 9, American Chemical Society, Washington, DC, US.

PCT International Search Report, PCT/NL2013/050381, dated Oct. 21, 1998.

*Primary Examiner* — Brian J Gangle
(74) *Attorney, Agent, or Firm* — TraskBritt, P.C.

(57) ABSTRACT

In one aspect the disclosure relations to means and methods for identifying a protein or a DNA encoding the protein, involved in the production of a product by a micro-organism. In the methods the micro-organism is cultured under different culture conditions each of which exhibit a different level of the product that is produced by the micro-organism. The genetic expression of the genes of the micro-organism is compared with the level of the product, and groups of DNAs are identified that are involved in the production of the product by the micro-organism.

20 Claims, 9 Drawing Sheets

SCREENING METHOD FOR MICRO-ORGANISMS AND METHODS FOR THE PRODUCTION OF A PRODUCT

CROSS-REFERENCE TO RELATED APPLICATIONS

This application is a national phase entry under 35 U.S.C. §371 of International Patent Application PCT/NL2013/050381, filed May 24, 2013, designating the United States of America and published in English as International Patent Publication WO 2013/176550 A1 on Nov. 28, 2013, which claims the benefit under Article 8 of the Patent Cooperation Treaty to European Patent Application Serial No. 12169178.6, filed May 24, 2012.

TECHNICAL FIELD

The disclosure relates to the field of microbiology. The disclosure in particular relates to methods for determining genes involved in the production of a product by a micro-organism. The identified genes can be transferred to a different micro-organism, for instance, for production purposes.

BACKGROUND

Micro-organisms produce many different products. Examples of such products are antibiotics, alkaloids and other secondary metabolites or proteins. The discovery of an activity of product(s) produced by the micro-organism is often the first step in the discovery of new medicaments or products for industrial or agricultural use. The discovery is typically followed by the characterization of the product(s) that cause the observed activity. Is the activity the result of one produced product or is the activity the result of the combined activity of several products? What chemical structure(s) is/are responsible for the observed activity? Is it proteinaceous or chemical, and what it is the chemical structure or amino-acid sequence of the proteinaceous molecule? This work typically takes a lot of time. Identification of the molecule(s) responsible for the activity is often only the first step in a long process from discovered activity to industrial or medical use of the molecules responsible for the activity.

BRIEF SUMMARY

The disclosure provides means and methods for rapidly identifying the gene(s) involved in the production of a product or products with an identified activity by a micro-organism. The genetic information retrieved can provide information on the identity of the product(s). Moreover, the responsible genes can be transferred to a different host for scalable production, if needed.

The disclosure now provides a method for identifying a protein or a DNA encoding the protein, involved in the production of a product by a micro-organism, the method comprising:

culturing the micro-organism under at least two different culture conditions and selecting from the at least two culture conditions at least two cultures/conditions in which the level of the product that is produced by the micro-organism is different, preparing a protein and/or RNA sample from the selected cultures of micro-organisms, determining a sequence of at least part of the proteins and/or RNA in the samples, selecting sequences of proteins and/or RNA of which the amount differs between the samples of the selected cultures of micro-organisms, grouping selected sequences of proteins and/or RNA coded for by DNAs located in a region of at least about 10 kb of the micro-organism genome (first cluster) into a group, grouping remaining selected sequences of proteins and/or RNA (if any) coded for by DNAs located in a different region of at least about 10 kb of the micro-organism genome (second cluster) into a further group, identifying a group of selected sequences of proteins and/or RNA that contains at least two different RNAs or proteins of which the amount correlates with the level of the product that is produced by the micro-organism under the at least two different culture conditions, and identifying a protein or DNA that comprises a sequence of the identified group, involved in the production of the product by the micro-organism.

Also provided is a method for identifying a protein or a DNA encoding the protein, involved in the production of a product by a micro-organism, the method comprising, culturing the micro-organism under at least two different conditions and selecting from the conditions at least two cultures in which the level of the product that is produced by the micro-organism is different, preparing a protein and/or RNA sample from the selected cultures of micro-organisms, determining a sequence of at least part of the proteins and/or RNA in the samples, selecting sequences of proteins or RNA of which the amount differs between the samples of the selected cultures of micro-organisms, grouping selected sequences of proteins or RNA coded for by DNAs into a group that comprises selected sequences that are separated by no more than 30 open reading frames (ORFs) on the genome of the micro-organism (first group), optionally grouping remaining selected sequences of proteins or RNA coded for by DNAs (if any) into a further group that comprises selected sequences that are separated by no more than 30 open reading frames (ORFs) on the genome of the micro-organism group (second group), identifying a group of selected sequences that contains the coding regions of at least two different RNAs or proteins of which the amount correlates with the level of the product that is produced by the micro-organism under the at least two different conditions, and identifying a protein or DNA that comprises a sequence of the identified group involved in the production of the product by the micro-organism.

Also provided is a method for identifying a protein or a DNA encoding the protein, involved in the production of a product by a micro-organism, the method comprising:

culturing the micro-organism under at least two different conditions and selecting from the conditions at least two cultures in which the level of the product that is produced by the micro-organism is different, preparing a protein and/or RNA sample from the selected cultures of micro-organisms, determining a sequence of at least part of the proteins and/or RNA in the samples, selecting sequences of proteins or RNA of which the amount differs between the samples of the selected cultures of micro-organisms, grouping selected sequences on the basis of their location on genome of the micro-organism of interest, identifying a group of selected sequences that contains the coding regions of at least two different RNAs or proteins of which the amount correlates with the level of the product that is produced by the micro-organism under the at least two different conditions, and identifying a protein or DNA that comprises a sequence of the identified group involved in the production of the product by the micro-organism.

Grouping of selected sequences is done on the basis of their location on genome of the micro-organism of interest. Selection can be done on the basis that the selected sequences are located in a region of at least about 10 kb of the genome of the micro-organism. Alternatively the selection can be done on the basis of the number of open reading frames that separate selected sequences on the genome of the micro-organism. In the latter case selected sequences of proteins or RNA coded for by DNAs are preferably grouped such that the group comprises selected sequences that are separated by no more than 30 open reading frames (ORFs) on the genome of the micro-organism (first group). It is preferred that remaining selected sequences of proteins or RNA coded for by DNAs (if any) are grouped such that the group comprises selected sequences that are separated by no more than 30 open reading frames (ORFs) on the genome of the micro-organism (second group). A group, thus, contains selected sequences that are separated by no more than 30 ORFs on the genome of the micro-organism. Preferably, they are separated by no more than 20 ORFs on the genome of the micro-organism. Preferably, they are separated by no more than 10 ORFs, preferably by no more than five ORFs. In a preferred embodiment, at least two of the selected sequences within a group are separated by no more than 30, preferably by no more than 20, preferably no more than 10, preferably no more than 5 ORFs on the genome of the micro-organism. In a particularly preferred embodiment, the at least two selected sequences are, or are encoded by, ORFs that are adjacent to each other on the genome of the micro-organism. The selected sequences in one or further groups are preferably selected such that the selected sequences in the resultant group are separated by the hereinabove mentioned number of ORFs. Once a group contains two selected sequences further selected sequences can be added to the group, provided that the added selected sequences meet the grouping criteria. A group, thus, contains two, three, four, five or more selected sequences. A group comprising at least two selected sequences that are separated by no more than 30 ORFs may contain one or more further selected sequences that have more than 30 intervening ORFs with respect to the earlier selected sequences, as long as each of the selected sequences in the group is separated by no more than 30, preferably no more than 20, 10, 5 ORFs. A group does not have to contain all of the selected sequences that are located in the same region of the genome of the micro-organism. Accuracy may increase with increasing numbers of selected sequences in the group.

Groups span a region of DNA on the genome of the micro-organism. Groups that contain more than two selected sequences by default contain at least one, and in most cases at least two selected sequences that are located closest to an ORF that is not in the region that is spanned by the group. Selected sequences are preferably grouped such that these outward most selected sequences are the sequences that are separated by no more than 30, preferably no more than 20, 10, 5 ORFs. A sequence, be it selected or not that is located outside the region on the micro-organism that is spanned by the group can functionally belong to the group of selected sequences, i.e., be involved in the same biological process.

A selected sequence is preferably a sequence of which the amount correlates with the level of the product that is produced by the micro-organism under the at least two conditions. Preferably all of the selected sequences are sequences of which the amount correlates with the level of the product.

Different groups differ from each other at least in the presence (or absence) of one ORF or selected sequence. The different groups typically differ from each other in at least 10 ORFs. Selected sequences of proteins or RNA coded for by DNAs are preferably grouped on the basis that they are separated by no more than 20 open reading frames (ORFs) on the genome of the micro-organism. Remaining selected sequences of proteins or RNA coded for by DNAs (if any) are grouped on the basis that they are separated by no more than 20 open reading frames (ORFs).

Different groups are typically, though not necessarily, located on different contigs. Different groups are typically located at different genomic locations. The different groups typically, but not necessarily do not contain the same ORFs.

A group typically contains at least two selected sequences. In a preferred embodiment, the group contains at least three selected sequences, more preferably a group contains at least 5 selected sequences. In a preferred embodiment, the at least three and preferably at least five selected sequences are sequences of which the amount correlates with the level of the product that is produced by the micro-organism under the different culture conditions. In a preferred embodiment, a group contains all of the selected sequences that qualify the criteria for allocating the selected sequence to the group.

The micro-organism that is cultured under one condition can be a genetic variant from the micro-organism that is cultured under the second culture condition. In such a case a difference between the culture conditions is the presence of the different genetic variants in the cultures. The culture medium or other growth conditions can be the same between the different culture conditions. Genetic variants typically contain the same genomic DNA but for a mutation in 1-5 genes. A mutation in the variant is typically a mutation that inactivates the gene. The gene is typically a control gene that controls the expression of a number of different genes. A non-limiting example of such a gene is the dasR gene.

A method of the disclosure is particularly suited to rapidly identify a gene or protein involved in the production of a product or products. The identity of the DNA or protein can provide information on the nature of the produced product. The identification can also be the start of the cloning of the gene encoding the protein or comprising the DNA encoding the protein. The coding region of the gene can subsequently be analyzed and/or transferred to a different micro-organism. The DNA encoding the protein is preferably the coding region of the protein. In a particularly preferred embodiment, the DNA encoding the protein is a gene comprising the coding region for the protein. A gene contains the DNA encoding the protein together with cis-acting sequences necessary for transcription of the protein coding region. An example of such a cis-acting sequence is a promoter.

The product is preferably a chemical compound or a protein. A chemical compound is herein defined as a compound comprising two or more atoms and that is not a protein. It encompasses organic chemical compounds and peptides. Peptides are polymers of amino acid monomers linked by peptide bonds. The shortest peptide is a dipeptide consisting of two amino acids joined by a single peptide bond. The art is ambiguous on maximal length of a peptide, i.e., when is a peptide no longer a peptide but a polypeptide or protein. In the disclosure a peptide has a maximum length of 50 amino acids. Longer amino acids polymers comprising 51 or more amino acid monomers linker by peptide bonds are considered polypeptides or proteins. The term polypeptide and protein are herein used interchangeably. A peptide and the protein may contain modifications. Proteins are typically produced by translation of an RNA by ribosomes. Peptides are often also produced by this process. However, some peptides, notably the nonribosomal peptides, are not produced by ribosomes. Nonribosomal peptides (NRP) are a class of peptide secondary metabolites, usually produced by microorganisms like bacteria and fungi. Nonribosomal peptides are also found in higher organisms, such as nudibranchs, but are thought to be made by bacteria inside these organisms. The nonribosomal peptides are one example of a wide range of peptides that are not synthesized by ribosomes. While ribosome synthesized peptides are typically linear, the peptides that are not synthesized by ribosomes can have a cyclic and/or branched structures, can contain non-proteinogenic amino acids including D-amino acids, carry modifications like N-methyl and N-formyl groups, or are glycosylated, acylated, halogenated, or hydroxylated. Cyclization of amino acids against the peptide "backbone" is often performed, resulting in oxazolines and thiazolines; these can be further oxidized or reduced. Peptides that are not synthesized by ribosomes can be dimers or trimers of identical sequences chained together or cyclized, or branched. Peptides that are not produced via translation of an RNA typically contain 50 or fewer amino acids linked together by a peptide bonds and considered to be a chemical compound irrespective of the number of amino acids monomers linked together via a peptide bond, they contain.

The product is preferably a metabolite or a protein. Preferred examples of proteins are enzymes such as a cellulase, a pectinase, a lipase, an amylase, a chitinase, a mannanase, a xylanase, a protease, a peroxidase, a catalase, a laccase, a sugar isomerase or another industrially relevant enzyme. Preferred examples of metabolites are antibiotics, anticancer agents, anthelmantics, antifungals, immunesuppressants, herbicides, alkaloids, anti-inflammatory agents, and antivirals. Any bioactive molecule can be linked to a gene or gene cluster using the technology of the disclosure, as long as its bioactivity can be distinguished and measured. Preferred examples of distinguishing features for a product are a band or peak determined by chromatography, electrophoresis or mass spectrometry, an enzymatic activity, an inhibition zone for bacterial growth or a color, such as associated with a pigment, and preferably one that can be discerned by spectrophotometry or colorimetry.

The product is preferably a secondary metabolite. Secondary metabolites typically are organic compounds that are not directly involved in the normal growth, development, or reproduction of an organism. Unlike primary metabolites, absence of secondary metabolites does not result in immediate death, but rather in long-term impairment of the organism's survivability, fecundity, or aesthetics, or perhaps in no significant change at all. Humans use some secondary metabolites as medicines. Micro-organisms produce a large variety of different secondary metabolites. (Berdy, Bioactive microbial metabolites, J. antibiot. 58:1-26). In a preferred embodiment, the secondary metabolite is an antibiotic, an antibiotic resistance inhibitor, an anti-cancer compound, an enzyme inhibitor, an antifungal, an antihelminthic, an immunostimulant, an immunesuppressant, an insecticide or a herbicide. In a preferred embodiment, the product has antimicrobial activity. A preferred class of antibiotic resistance inhibitors are compounds that increase the sensitivity to an antibiotic of a bacterium that is resistant to the antibiotic under physiological conditions. An example of such compound is clavulanic acid. Such products can, for instance, be evaluated by growing the product producing micro-organism in the presence of the resistant micro-organism. Different levels of product are reflected by different distances of the two micro-organisms from each other when grown in the presence of the antibiotic. In a particularly preferred embodiment, the secondary metabolite is an alkaloid or an antibiotic. Preferred antibiotics are antibiotics of the following groups:

aminoglycosides (e.g., kanamycin, neomycin, streptomycin), ansamycins, carbapenems, cephalosporins, glycopeptides (e.g., vancomycin, teichoplanin, daptomycin), lantibiotics (e.g., actagardin, mersacydin, nisin), lincosamides (e.g., clindamycin, lincomycin), macrolides (e.g., azithromycin, erythromycin, spectinomycin), penicillins (ampicillin, methicillin, penicillin G), polypeptides (e.g., bactitracin), quinolones (e.g., cirpofloxacin, nalidixic acid), rifamycins (e.g., rifampicin), sulfonamides (e.g., trimethoprim), tetracyclins, tuberactinomycins (e.g., capreomycin, viomycin), and chloramphenicol.

Many different micro-organisms produce enzymes and metabolites. Preferred micro-organisms for the methods of the disclosure are bacteria, fungi, archaea, and protists; microscopic plants (green algae); and microscopic animals such as plankton and the planarian. In a preferred embodiment, the micro-organism is an actinomycete or *Actinobacterium*, preferably a streptomycete or *Streptomyces* bacterium. These types of micro-organisms are a particularly rich source of products of which many still remain to be discovered.

A method of the disclosure is particularly suited for situations wherein the identity of the product is not known prior to performing the method of the disclosure. The method requires that the activity can be measured and that the level or amount of activity can be determined in different culture conditions, at least relative to each other. Products that are produced by micro-organisms often require the concerted expression of a number of different genes. One of the ways in which micro-organisms have solved the problem of concerted expression is the grouping or clustering of genes at the same location of the genome. The grouping may also facilitate lateral gene transfer of the cluster, to provide another micro-organism with the same functionality. An example of such a grouping or cluster is a group or cluster of genes involved in the production of an antibiotic. In this case the genes involved in the production and in generating self-resistance to the antibiotic are located in the same chromosomal region. Other examples of such a grouping or cluster include genes for sugar transport systems, for transporters for small peptides and other small molecules, and for primary and secondary metabolism pathways.

The method of the disclosure can identify proteins and/or DNA encoding proteins involved in the production of the product by their concerted expression. Specifically for micro-organisms it was observed that the grouping by chromosomal location facilitates the identification of the protein and/or the DNA encoding the protein involved in the production of the product. Many micro-organisms contain genetic information that could in potential code for a large number of antibiotics. Many of the potential antibiotic coding regions are normally not expressed. This relatively large coding potential makes the identification of the genes or proteins responsible for the production of a particular activity or property tedious. Using a method of the disclosure, however, such proteins or DNAs encoding the proteins can rapidly be identified. Moreover, since the region is involved in the production of the product is now known, other genes in the same location, but of which the level of expression is not concerted, can be tested for their involvement in the production of the product. Candidate genes in the selected group can be tested individually for their involvement in the production of the product.

A method of the disclosure is also suited for the identification of proteins or DNAs encoding the proteins that are involved in the production of primary metabolites and enzymes. For instance, a protease is typically encoded by a single coding region, but varying the activity of the protease produced by the micro-organism can require concerted expression of the gene encoding the factor controlling the expression of the protease, genes required for efficient export of the protease, etc. Another example is an enzyme inhibitor such as a beta-lactamase inhibitor protein (BLIP), which may be co-expressed together with a beta lactam-type antibiotic.

The process is advantageous when at least two culture conditions are selected wherein the level of production of the product by the micro-organism is different. The selected cultures and/or culture conditions can be a culture/condition wherein the production of the product is absent or at least undetectable and a culture/condition wherein the product is produced by the micro-organism. The accuracy of the method increases with the selection of at least one further culture/condition in which the product is produced at a level that is different from the other selected cultures/conditions. It is preferred that at least three cultures/conditions are selected. The accuracy of a method of the disclosure increases with the selection of further cultures/conditions wherein the level of production of the product is different between the selected cultures/conditions. Thus, in a preferred embodiment at least three cultures are selected in which the level of the product or activity that is produced by the micro-organism is different in the different culture conditions. The different levels of the product preferably reflect different levels of production. In a preferred embodiment, the levels differ at least 1.5-fold between each of the cultures/conditions. Preferably at least one of the levels differs at least 3-fold from the level of another selected culture/condition, wherein both levels are above the detection limit. In a preferred embodiment of the disclosure, three cultures/conditions are selected wherein the level of the product is different among the three selected cultures/conditions, in this embodiment it is preferred, but not necessary that in one of the selected cultures/conditions the level of the product is zero or below the detection limit.

The level of the product or activity that is produced by the micro-organism can be determined by measuring the amount of product produced at a certain time point after initiation of the culture. The amount of product produced can be determined or inferred, for instance, as the activity of the product in an assay or as a pigment or odor. The level or amount of the product can be determined as such, or preferably be determined relative to the level/amount or activity in the other selected cultures/conditions.

The protein or RNA sample can be prepared from the cultured micro-organisms, from the culture medium wherein the micro-organism were cultured or both. Although some RNA is present in the culture medium, for instance, from lysed micro-organisms, the culture medium is typically used to prepare protein samples. A protein sample can be prepared from micro-organism, culture medium or both. The proteins, the RNA or both are subsequently subjected to a step wherein sequence information is obtained from at least part of the proteins or RNAs in the sample. The sequence information should be sufficient to identify the coding region of the protein or RNA in the genome of the micro-organism. The amount of sequence information needed per RNA or protein depends among others on the coding region and the amount of sequence identity it contains with other coding regions in the genome. Typically, it is sufficient to determine the sequence of 50 consecutive nucleotides in a given RNA or two sections of 8 consecutive amino acids in a given protein. In a preferred embodiment, the sequence of at least 100 consecutive nucleotides is determined for a given RNA or the sequence of at least four sections of 8 consecutive amino acids is determined for a given protein. Sequence information on protein or RNA can be obtained using a variety of different methods. RNA sequences are typically determined using Whole Transcriptome Shotgun Sequencing or RNA-Seq, whereby cDNA is sequenced using next-generation sequencing technology to get information about a sample's RNA content, or using DNA microarrays that contain probes for specific genes in the genome of the micro-organism. As the hybridization of the RNA, or cDNA produced therefrom, is specific for the probe sequence the sequence can be inferred from the hybridization pattern on the DNA microarray. For protein determination, in a preferred embodiment, enzymatic digestion of the proteins using trypsin, chymotrypsin or another protease is used, followed by mass spectrometry to link the obtained peptides to a database cataloguing the predicted masses of all possible peptides and their fragmentation products that may be generated from the genome of the organism of interest. The sequence of the detected peptide can be determined by detecting mass correspondence between the detected peptide and a peptide in a database and mass correspondence between the fragmentation products of the detected peptide and the fragmentation products of a peptide in a database.

In a further step of a method hereof, a measure for the amount of protein and/or RNA is determined. The protein and/or RNA of which the sequence is determined or is to be determined is preferably quantified. The measure or quantification can be the determination of the absolute amount of the specific protein or RNA in the sample. However, it often suffices to determine the amount relative to one or more reference proteins or RNAs in the sample.

For proteins and RNAs of which a sequence or mass was obtained that was sufficient to localize the position of the coding region on the genome, the genome positions are identified. The method of the disclosure works best when sequence information, sufficient to localize the coding region on the genome, is obtained for the proteins and/or RNAs in the sample. Preferably, such information is obtained for at least 50% of the proteins and/or RNAs in the sample. In an even more preferred embodiment, such information is obtained from at least 90% of the proteins and/or RNAs in the samples.

Subsequently, sequences of protein and/or RNA of which the amount differs between the samples of the selected cultures of micro-organisms are selected. It is not required that all sequences of which the amount differs are selected. Selection may comprise a part of the sequences of which the amount differs. Sequences are preferably selected on the basis that the amount correlates with the level of the product that is produced by the micro-organism under the different conditions.

The selected sequences are grouped on the basis of their location on the genome of the micro-organism. For this aspect it is important that sequence information is available for at least a significant part of the genome of the microorganism. Preferably, more than 40% of the sequence of the genome of the micro-organism is known. Preferably, at least 50%, more preferably at least 70% and in a particularly preferred embodiment at least 90% of the sequence of the genome of the micro-organism is known. If the sequence information of the genome is not available from a database, it can be generated de novo. Genome sequencing is presently a routine technique and most, if not all, micro-organisms can be sequenced without much effort. It is often not necessary to sequence the entire genome of the micro-organism. For instance, Streptomyces species possess a single linear chromosome consisting of a conserved core flanked by two non-conserved arms. The arms of the chromosome contain largely acquired DNA and are the location of most contingency genes, including those that code for nonessential functions, such as secondary metabolite production. Thus, for Streptomyces species, it is, depending on the type of activity that is analyzed, for instance, an antibiotic, often sufficient to obtain the sequence of the arms flanking the conserved core. The sequence information can be present as a reconstruction of the genome, or present as a so-called contig. A contig is a set of overlapping DNA segments that together represent a contiguous region of DNA. In bottom-up sequencing projects, a contig refers to overlapping sequence data (reads); in top-down sequencing projects, contig refers to the overlapping clones that form a physical map of the genome that is used to guide sequencing and assembly. Contigs can, thus, refer both to overlapping DNA sequence and to overlapping physical segments (fragments) contained in clones depending on the context. For the disclosure, it is preferred but not required, that the contig is a complete representation of the genome of the micro-organism. However, complete coverage and complete knowledge of the location of contigs relative to each other is not necessary as long as the contigs are sufficiently long to encompass a group of selected sequences. This is typically the case when a contig contains a consecutive sequence of at least 10 kb. In a preferred embodiment, a contig contain a consecutive sequence of at least 30 kb and in an even more preferred embodiment of at least 100 kb. One contig can contain one or more groups of selected sequences. The groups or clusters of selected sequences may partially overlap. A contig typically contains two or more open reading frames (ORFs). A region of the genome of the micro-organism comprising DNAs coding for proteins or RNAs is preferably a chromosomal region. Such a chromosomal region preferably spans a consecutive stretch of at least about 10 kb on a chromosome of the micro-organism. A chromosomal region preferably spans a consecutive stretch of at least about 20 kb on the genome. In a particularly preferred embodiment, the chromosomal region spans a consecutive stretch of at least about 50 kb on the genome of the micro-organism. A chromosomal region typically does not contain a consecutive stretch of more than 50 kb on the genome of a micro-organism. The grouping of selected sequences into a group or cluster is done on the basis of the location of the DNA coding for the selected sequences relative to each other. The DNAs coding for selected sequences that are grouped into a group or cluster, according to the disclosure, are located in the same region of the genome of the micro-organism. The size of the chromosomal region is indicated hereinabove. The one or more regions on the genome may be consecutive or (partly) overlap. When, in a method of the disclosure, two or more chromosomal regions are defined, they each differ from each other defined chromosomal region by at least one coding region. As each chromosomal region reflects a continuous stretch of DNA on the genome of the micro-organism, the at least one coding region by which any two defined chromosomal regions differ from each other is always located to the left or right of one of the defined chromosomal regions. Chromosomal regions can be arbitrarily defined or defined on the basis of the nature and/or sequence of the coding regions, on the genome of the micro-organism or be defined by a combination thereof. An example of defining chromosomal regions on the genome on the basis of the nature and/or the sequence of the coding regions is a definition on the basis of sequence homology to a known chromosomal region or cluster of genes. Such a known region or cluster of genes can, for instance, be a cluster of genes that are known to be collectively involved in the production of an antibiotic. Those selected sequences are grouped on the basis of their location on the genome, does not mean that all coding regions in that chromosomal region code for selected sequences proteins or RNA. The chromosomal region can also contain one or more coding regions that do not code for a selected sequence.

The method further comprises the identification of a group of selected sequences (or cluster) that contains the coding regions for at least two different RNAs or proteins of which the (preferably quantified) amount correlates with the level of the product that is produced by the micro-organism under the at least two different conditions. The amount of product correlates with the amount of RNA or protein when the both amounts show the same directional change in the different culture conditions. When, for example, the selected cultures/conditions include a culture/condition wherein no product could be detected and a culture/condition wherein the product is detected, then correlating RNAs and proteins have a level that follows the same pattern, e.g., low or undetectable in the first condition and higher or detectable in the second condition, or vice versa. In another example, when, for instance, the two culture conditions elicit different levels of the product, then the correlating RNAs or proteins are detectable in both conditions and the levels are higher in the culture condition eliciting the higher level of product. The correlation improves if not only the trend of amounts is the same for the product and the RNAs or proteins in the different conditions, but also the relative ratios are the same or similar. In other words, if the ratio between the level of the product between the different culture conditions is 3, the ratio of the correlating RNAs or proteins between the different culture conditions is also around 3. However, such an exact correlation is often not attainable due to other factors that affect the detected levels. For instance, the product or the RNAs/proteins may have different stability, there may be a difference in the timing of the presence of the RNA/protein and the product, there may be measured differences due to the fact that the sample contains micro-organisms that do not contribute to the production, etc.

An identified group(s) is/are likely to contain coding regions that are involved in the production of the product of interest. The accuracy with which the group containing coding regions that are involved in the production of the product is identified can be increased by analyzing the sequence of the selected sequences or the regions encoding them and/or comparing the selected sequences or the regions encoding them with sequence databases and comparing the function of the database hits with the properties of the product. The grouping and subsequent identification also generates information on the chemical nature of product that is produced. The characteristics of the coding regions can, for instance, indicate that the product is a non-ribosomal peptide, a beta-lactam antibiotic, an actinomycin-producing cluster or the like. Members of the identified group are coding regions that code for proteins and RNAs involved in the production of the product by the micro-organism. The identified members can subsequently be cloned and, for instance, transferred to a different micro-organism.

A method hereof is, as mentioned hereinabove, particularly suited to identify proteins or RNAs involved in the production of a product of which the activity is observed, but wherein the nature of the product is (largely) unknown. It is an advantage of a method of the disclosure that genes involved in the production of the product having the activity can be identified even when extensive knowledge of the characteristics and structure of the product is absent. This feature can advantageously be used to rapidly screen a library of micro-organisms for the production of a new and previously unidentified product. The identified cluster of genes and coding regions therein are not only useful for cloning and insertion into a suitable production micro-organism, but also provides information on the characteristics and structure of the product. When the product is a secondary metabolite, the identified cluster or coding regions therein can give information on the nature of the secondary metabolite. This can be useful when looking for a specific variant of an antibiotic, or even when looking for an as yet unknown type of antibiotic. In a preferred embodiment, a method hereof further comprises identifying the product of interest.

The identification of the protein or DNA that comprises a sequence of the identified group involved in the production of the product by the micro-organism also leads to the identification of the associated gene in the genome of the micro-organism. This gene can be cloned and inserted into a different micro-organism. This can be done to study the function of the gene further or to have the product produced by the recipient. In a preferred embodiment, a method, therefore, further comprises isolating the identified gene(s) or coding region from the genome of the micro-organism. Preferably, the method further comprises providing a micro-organism of a different specifies with the identified gene or coding region. In a preferred embodiment, the different micro-organism is a strain of the same genus. In another preferred embodiment, the different micro-organism is a micro-organism of the same species, but a different strain, preferably a strain that has favorable properties when cultured on a large scale. In a preferred embodiment, the method further comprises providing the different micro-organism with genes or coding regions of the gene cluster comprising the identified gene or coding region. This micro-organism can be used to produce the product on a large scale. Preferred organisms of choice for the heterologous production of compounds or proteins obtained from actinomycetes are *Streptomyces lividans* for enzyme production and *Streptomyces coelicolor, Streptomyces lividans, Streptomyces rimosus* or *Streptomyces venezuelae* for the production of antibiotics and other natural products. In another preferred embodiment, enzymes may be expressed in *Bacillus*, in *Escherichia coli*, in *Aspergillus*, in *Pichia* or in *Trichoderma*. Thus, in a preferred embodiment, a method of the disclosure further comprises culturing the micro-organism, the different micro-organism or the micro-organism of a different species comprising genes or coding regions of the gene cluster comprising the identified gene or coding region. The disclosure further provides a method for obtaining a product produced by a micro-organism, the method comprising performing a method as previously defined herein and producing the secondary metabolite by the micro-organism or the micro-organism of a different species comprising the genes of the gene cluster comprising the identified gene and obtaining the produced product. The coding regions or genes providing to the different micro-organism can have the same nucleic acid sequence as found in the donor, or be adapted so as to express the same proteins but are different to accommodate codon usage in the recipient micro-organism. The coding regions may further be provided with other nucleic acids, such as promoters and the like for efficient expression in the recipient micro-organism. The coding regions may also be mutated, for example, to remove or modify a repressor or operator sequence that suppresses the expression of the product of interest. Part of the coding region may also be replaced by a similar but sufficiently distinct nucleic acid, for example, a module of the gene cluster for a polyketide antibiotic or a lantibiotic. In this way, combination of gene clusters may be achieved that allow the production of hybrid or modified antibiotics.

The advent of genome sequencing has revealed that many micro-organisms contain the genetic information to produce a large number of different secondary metabolites. This was a surprising finding as under standard conditions none or only a few of these are actually expressed by the micro-organism. It was, therefore, unknown whether this silent genetic information reflected true coding potential or reflected largely inoperative remnants. In the disclosure, it was found that at least some of these previously silent genes can be activated under appropriate culture conditions. This lead to the hypothesis that indeed this coding potential for secondary metabolites reflects a repertoire at the disposal of the micro-organism when the appropriate conditions occur. It has been found that indeed a large number of different conditions can be found wherein one or the other silent gene or number of genes are activated. In one embodiment, a method of the disclosure preferably comprises culturing the micro-organism under conditions that differ from each other in that the culture medium has a different pH at the start of the culture, differ in the presence, amount and/or type of soil in the culture, differ in the presence, amount and/or type of bacterial remains at the start of the culture, differ in amount or type of carbon source in the culture medium, in the amount or type of nitrogen source in the culture medium, differ in the metal composition, differ in the presence, amount and/or type of a further micro-organism in the culture, differs in the temperature, and/or differ in the presence of a signal molecule such as N-acetylglucosamine (GlcNAc).

We here use antibiotics as an example, although the technology works on any molecule, such as an enzyme or a secondary metabolite that has a detectable biological activity. Using this knowledge, several bacterial strains were identified that produce interesting candidate antibiotics, and preferably under specific growth conditions. For production purposes (as well as for patent purposes) it is necessary to identify the genes that are responsible for the production of the new antibiotic. This was previously done using rather cumbersome and roundabout methods, e.g., following rounds of directed and/or random mutagenesis. Actinomycetes typically have many PKS (polyketide synthase) or NRPS (nonribosomal peptide synthase) type antibiotics so that identification of the gene cluster of interest is very difficult. Additionally, for truly novel antibiotics the gene (cluster) will be unknown. The presented technology will discover the genes for such completely new antibiotics with equal efficiency as those for antibiotics belonging to known classes of molecules.

In one aspect the system exploits the application of genome sequencing by combining the following technologies:

1. (Rough) genome sequence and derived protein database (based on single sequencing run of $500 for bacterial genomes)
2. Metabolite identification under different growth conditions.
3. Activity assay, e.g., pigmentation, antibiotic activity or antitumor activity.
4. proteomics or RNA-seq to assess the changes in the protein or RNA expression profiles under the same conditions.

The expression profile of the (generally very large and hence easy to identify) proteins is then matched to that of the secondary metabolites and the measured bioactivity under all growth conditions. This allows identification of product, bioactivity and protein. The protein then connects directly to the genome. The large biosynthetic proteins whose expression profile is the same as that of the antibiotic.

The method significantly accelerates the identification of genes that are responsible for the production of any bioactivity (antimicrobial, anticancer, antifungal, antiherbicide, enzyme) that can be measured and whose activity fluctuates with growth conditions.

A method hereof is also very suitable for the identification of enzymes, as often there may be many enzymes of a certain class and it can be difficult to isolate the responsible protein to allow amino acid sequencing.

EXAMPLES

Methods

Strains and Growth Conditions

Figure 1:
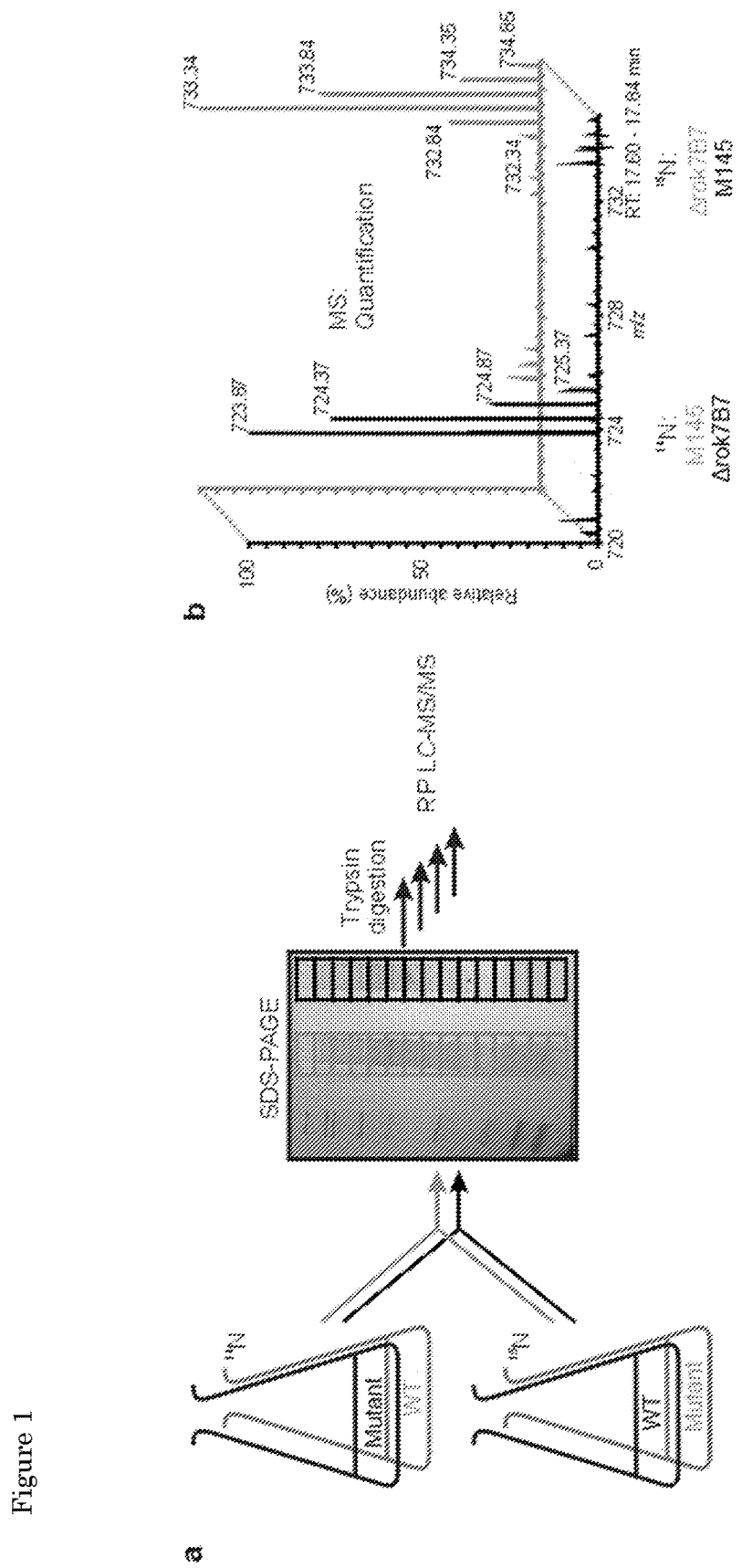
FIG. 1: Experimental approach for quantitative proteomics of the dasR and rok7B7 deletion mutants. Mutant and parent (WT) strain were grown in either $^{14}$N or $^{15}$N labeled cultures, and mixed for SDS-PAGE separation (a). Bands from SDS-PAGE gel were digested using trypsin and subjected to LC-MS/MS analysis. A typical MS spectrum for one peptide is shown (b). The label swap experiment is shown in grey.

*Streptomyces coelicolor* A3(2) M145 was obtained from the John Innes Centre strain collection. The dasR null mutant (SAF29) (Rigali et al., 2006) and rok7B7 null mutant (GAM33) (Swiatek et al., 2013) of wild-type *S. coelicolor* were described previously. *B. amyloliquefaciens* HIL-Y85/54728 was obtained from Novacta Biosystems (Welwyn Garden City, UK). *Streptomyces* strains Che1 and HM151 were obtained de novo from soil samples. All *Streptomyces* strains were grown as indicated according to routine methods (Kieser et al., 2000).

*S. coelicolor* M145 and its congenic dasR and rok7B7 deletion mutants were grown in adapted NMMP medium for $^{14}$N/$^{15}$N-labeling (Swiatek et al., 2013). Samples were taken at late logarithmic phase when production of pigmented antibiotics became apparent. $^{14}$N/$^{15}$N-labelling experiments were performed in duplicate with a label swap to avoid that differences in media composition should affect the outcome of the proteomics experiments.

A seed culture of *B. amyloliquefaciens* was grown in Tryptic Soy Broth (TSB) for 24 h as described (Appleyard et al., 2009), before transfer (1:50 (v/v)) to mersacidin production medium, LB, or fresh TSB. Cultures were grown for five days at 30° C. Proteomics samples were taken after 24 h as protein levels were too low after five days of growth.

*Streptomyces* strains Che1 and HM151 were grown in liquid NMMP medium containing 1% (w/v) glycerol and 0.5% (w/v) mannitol as carbon sources for 4-6 days, using five different additives to create varying growth conditions: (−), no additive, (A) NaOH to pH 9, (B) 25 mM N-acetylglucosamine, (C) 0.8% (w/v) Bacto peptone (Difco), (D) 0.5% (w/v) Bacto yeast extract (Difco), (E) 1 (HM151) or 2% (Che1) (w/v) NaCl. For antibiotic activity assays, *Micrococcus luteus* was spread on LB agar plates and 20 µL, spent medium were placed on the plates. After growth at 30° C. 0/N, the growth inhibition zone was measured.

MALDI-ToF MS Analysis

In case of prefractionation of compounds, supernatants were acidified by adding trifluoroacetic acid to a concentration of 0.1% (v/v), and loaded on a Sep-Pak plus C18 cartridge (Waters). Stepwise elution was performed using 1 mL of 0-90% (v/v) acetonitrile in 0.1% (v/v) TFA. Fractions were concentrated using a vacuum concentrator. Spent medium or concentrated fractions were mixed 1:1 (v/v), or 1:10 (v/v) in case of *B. amyloliquefaciens* spent medium, with a saturated α-cyano-4-hydroxycinnamic acid solution in 50% (v/v) acetonitrile/0.05% (v/v) trifluoroacetic acid, 1 µL was spotted on a MALDI target plate, and samples were measured on a Bruker microflex LRF mass spectrometer in the positive ion reflectron mode using delayed extraction. For each spectrum, at least 1,000 shots were acquired at 60 Hz.

Illumina Sequencing

Illumina/Solexa sequencing on Genome Analyzer IIx was outsourced (ServiceXS, Leiden, the Netherlands). Hundred-nucleotide paired-end reads were obtained. Quality of the short reads was verified using FastQC located on the World Wide Web at bioinformatics.bbsrc.ac.uk/projects/fastqc/. Reads were trimmed to discard base-calls of low quality and filtered data were assembled using Velvet (Zerbino & Birney, 2008). The resulting contigs were analyzed using the GeneMark.hmm algorithm with the *S. coelicolor* genome as model for ORF finding (Lukashin & Borodovsky, 1998).

Proteomics Sample Preparation

Mycelia or *Bacillus* cells were harvested by centrifugation, washed, and sonicated for 5 min at 12 W output power using 5 s on/5 s off intervals in 100 mM Tris/HCl (pH 7.5), 10 mM $MgCl_2$, 5 mM dithiothreitol (DTT). Debris was removed by centrifugation at 16,000 g for 10 min at 4° C. Protein concentration of the extracts was determined using a Bradford protein assay, using BSA as standard.

$^{14}$N-labeled and $^{15}$N-labeled mycelial extracts were mixed 1:1 for protein content, and proteins separated on SDS-PAGE, followed by in gel-digestion, all as described (Swiatek et al., 2013). In-solution digestion and dimethyl labeling of Che1, HM151, and *Bacillus* extracts were performed as described (Gubbens et al., 2012), using 0.167 mg of total protein per sample. Labeled peptides were mixed 1:1:1 to yield mixtures containing 0.5 mg of protein each. Acetonitrile was removed using a vacuum concentrator and peptides were dissolved in 0.6 mL SCX buffer A for fractionation by Strong Cationic Exchange (SCX) on a polysulfoethyl A column (PolyLC, 100×2.1 mm, particle size 5 µm, average pore size 200 Å, column volume (CV) 0.346 ml). Mobile phases were: SCX A (10 mM $KH_2PO_4$, 20% acetonitrile, pH 3) and SCX B (10 mM $KH_2PO_4$, 20% acetonitrile, 0.5 M KCl, pH 3). Peptides were fractioned at a flow rate of 250 µl/min with a gradient of 0-18% SCX B in 18 CV (HM151) or 30 CV (Che1), 18-30% SCX B in 6 CV, and 30-100% SCX B in 5 CV. In total, 24 (HM151) or 32 (Che1) peptide fractions were collected for LC-MS analysis.

LC-MS/MS Proteomics Analysis

LC-MS/MS analysis on an LTQ-Orbitrap (Thermo, Waltham, Mass.) for both gel-extracted peptides ($^{14}$N/$^{15}$N labeling) (Florea et al., 2010) and SCX fractions (dimethyl labeling) (Gubbens et al., 2012) was performed as described, respectively.

Data analysis of $^{14}$N/$^{15}$N labeled samples using MSQuant (Mortensen et al., 2010) has been described elsewhere (Swiatek et al., 2013). Data analysis of dimethyl labeled samples was performed using MaxQuant 1.2.2.5 (Cox & Mann, 2008) as described (Gubbens et al., 2012). For *B. amyloliquefaciens* HIL-Y85/54728, the *B. amyloliquefaciens* FZB42 complete proteome set (Uniprot 2012_10) with 98.5% sequence identity (Herzner et al., 2011), was appended with the ten mersacidin-producing proteins annotated for *B. amyloliquefaciens* HIL-Y85/54728 (Uniprot). For the *Streptomyces* strains Che1 and HM151, ORFs identified by Genemark.hmm were translated to obtain a protein database, and the two mixtures obtained for each strain were analyzed in one MaxQuant run. Normalized protein expression ratios were split in three equally-sized quantiles (up, unchanged, or down). Expression ratio filtering was based on selection of the expected quantile for each comparison.

NMR-Based Metabolomic Analysis

For each condition, 20 mL spent medium of five biological replicates was liquid-liquid partitioned using the same amount of EtOAc. This was repeated two times, after which the combined EtOAc fractions were evaporated by rotary evaporator at 40° C. and reconstituted in 1 mL of $CH_3OH$-$d_4$ (CortecNet, Voisins Le Bretonneux, France).

NMR parameters have been described previously (Kim et al., 2010). 1D-$^1$H NMR spectra, 2D J-resolved spectra as well as $^1$H—$^1$H homonuclear and inverse detected $^1$H—$^{13}$C correlation experiments were recorded at 25° C. on a Bruker 500 MHz DMX NMR spectrometer (500.13 MHz proton frequency) equipped with TCI cryoprobe and Z-gradient system. $CD_3OD$ was used for internal lock purposes. 128 scans of a standard one-pulse sequence with 30° flip angle for excitation and presaturation during 1.5 s relaxation delay with an effective field of $gB_1$=50 Hz for suppression of the residual $H_2O$ signal was employed. For heteronuclear multiple bond correlation (HMBC), spectra were measured on Bruker 600 MHz DMX NMR spectrometer (600.13 MHz for proton and 150.13 MHz for $^{13}$C frequency) equipped with cryoprobe. A data matrix of 300×2048 points covering 33201.9×6265.6 Hz was recorded with 256 scans for each increment. A relaxation delay of 1.5 s and a coherence transfer delay optimized for a long range coupling of 8 Hz were applied. Data was linear predicted to 600×2048 points using 32 coefficients prior to echo-anti echo type 2D Fourier transformation and a sine bell shaped window function shifted by p/2 in the F1 dimension and p/6 in the F2 dimension was applied. The final spectrum was obtained by magnitude calculation along the F2 dimension.

For data processing of multivariate data analysis $^1$H NMR were automatically reduced to ASCII files using AMIX (v. 3.7, Bruker Biospin). Spectral intensities were scaled to TMSP and reduced to integrated regions of equal width (0.04 ppm) corresponding to the region of d 0.3-d 10.00. The region of d 4.7-d 5.0 and d 3.28-d 3.34 were excluded from the analysis because of the residual signal of $H_2O$ and $CH_3OH$-$d_4$, respectively. Partial least square-discriminant analysis (PLS-DA) was performed with the SIMCA-P software (v. 13.0, Umetrics, Umeå, Sweden) with unit variance (UV) scaling methods.

Results

Filamentous micro-organisms are widely used as industrial producers of products such as antibiotics, anticancer agents, antifungicides and enzymes (Bennett, 1998, Demain, 1991, Hopwood et al., 1995). These organisms include the eukaryotic filamentous fungi (ascomycetes) and the prokaryotic actinomycetes (e.g., *Amycolatopsis, Nocardia, Thermobifido* and *Streptomyces*). The market capitalization for antibiotics and enzymes totals around 28 and 2 billion dollars per year, respectively. Once a product of interest has been discovered, it is typically a long and painstaking process to identify the gene (cluster) that codes for the biosynthetic machinery, in particular considering the large number of such clusters found in these bacteria. Therefore, a new method that allows the rapid linkage between gene (cluster) and product of interest is highly desirable from a biotechnological and cost perspective.

The proteomining concept we have developed is based on the analysis of the production of a compound or protein of interest under conditions where production fluctuates, and the analysis of the concomitant changes in global expression profiles of the mRNA and/or proteome pool. We demonstrated previously that DasR globally represses antibiotic production in actinomycetes, and that deletion of the dasR gene (SCO5231 on the *S. coelicolor* genome) results in the relieve of this repression, resulting in the enhanced production of natural products (Rigali et al., 2008, Craig et al., 2012). We recently noticed another regulator that is involved in the control of antibiotic production, namely Rok7B7, encoded by SCO6008 on the *S. coelicolor* genome (Swiatek et al., 2013). These genes form ideal targets in approaches to obtain global changes in the production of antibiotics and other natural products.

To study the effect of the global changes regulatory proteins DasR and Rok7B7 on protein expression, *S. coelicolor* M145 and its congenic dasR and rok7B7 deletion mutants were grown in liquid minimal media containing either $^{14}$N or $^{15}$N as the sole nitrogen source, until late logarithmic phase when production of pigmented antibiotics became apparent. All experiments were performed in duplicate with a label swap to avoid that differences in media composition should affect the outcome of the proteomics experiments (FIG. 1a). $^{14}$N and $^{15}$N-labeled proteins were extracted from the mycelium, mixed in a roughly 1:1 molar ratio, separated by SDS-PAGE, and in-gel digested with trypsin (FIG. 1a). Digests were analyzed by LC-MS/MS on an LTQ-orbitrap mass spectrometer with the orbitrap analyzer enabling high resolution quantitation of peptide intensity ratios (FIG. 1b). $^{15}$N-incorporation was 99% based on the shape of the isotopical envelope.

Figure 2:
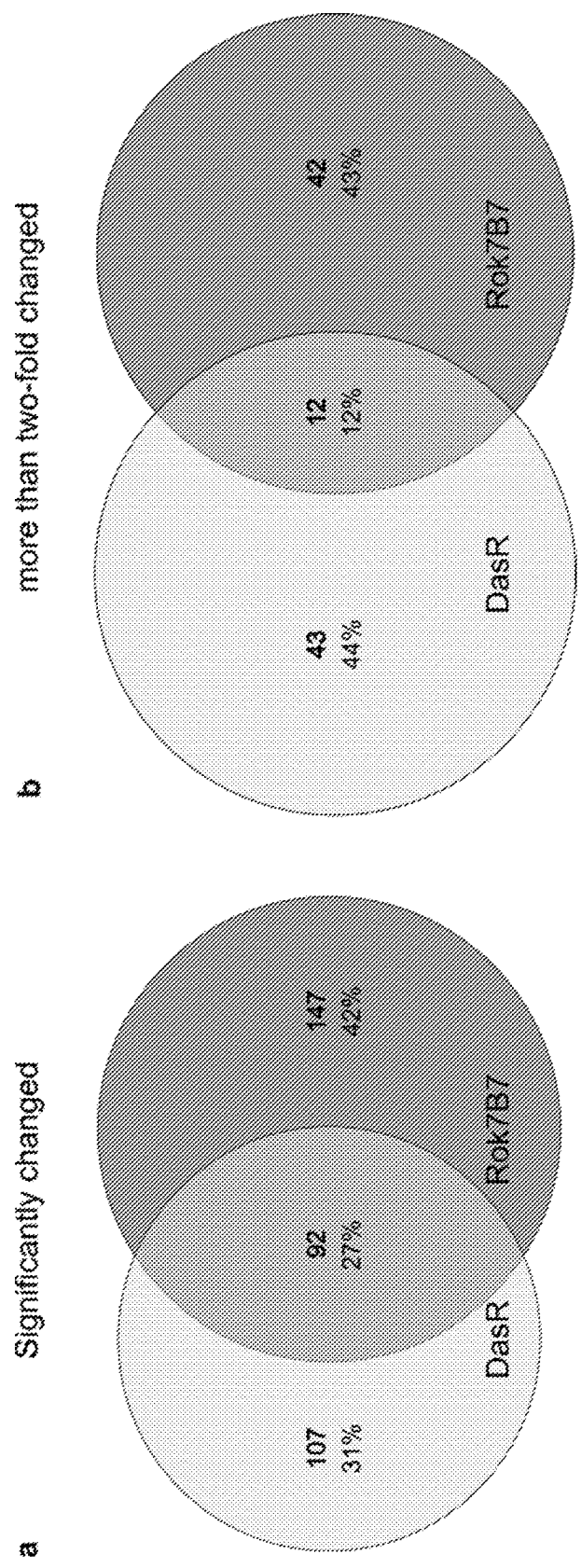
FIG. 2: Overlap of proteins that demonstrated significant changes in the dasR or rok7B7 null mutant as compared to the parent strain. Proteins were considered that demonstrated a statistically significant change (a) or proteins that demonstrated a statistically significant change of at least two-fold (b).

After elimination of all proteins that did not show the same response in the label swap, 346 proteins were found that demonstrate significantly changed levels in the dasR and/or rok7B7 null mutants (FIG. 2a). There is a substantial overlap between the significantly changed proteins in the dasR and rok7B7 deletion mutants (27%). However, when only the 97 proteins were considered whose levels changed at least two-fold, the overlap between both deletion mutants was reduced to only 11 proteins (FIG. 2b), whereas SCO3286 demonstrated opposite changes.

Excitingly, the most strongly differentially expressed proteins included a large number of proteins involved in secondary metabolite production (Table 1). Proteins involved in the production of calcium-dependent antibiotic (CDA; SCO3230-3232, SCO3236), for undecylprodigiosin and other prodiginins (SCO5878-5896, eight proteins detected), and for the production of a yet uncharacterized non-ribosomal peptide (SCO6431, SCO6436) demonstrated increased expression levels in the rok7B7 mutant. Surprisingly, deletion of dasR resulted in reduced expression of the biosynthetic machinery for these secondary metabolites. However, in line with the previously described repression of the cpk gene cluster by DasR (Rigali et al., 2008), expression of Cpk biosynthetic proteins (SCO6272-6292, seven proteins detected) was highly upregulated in the dasR mutant, and the same was observed for the rok7B7 mutant. Both mutants also demonstrated strongly increased expression of biosynthetic proteins for the siderophores coelichelin (SCO0492, SCO0494, SCO0498, and SCO0499, two- to five-fold upregulated) and desferrioxamine (SCO2782 and SCO2785, two to eight-fold upregulated). These compounds bind extracellular iron, allowing their import via dedicated ABC transporters (Barona-Gomez et al., 2006, Patel et al., 2010). A component of one of these transporters, CdtC (SCO7400) was also upregulated (two- to three-fold) in both mutants.

Figure 3:
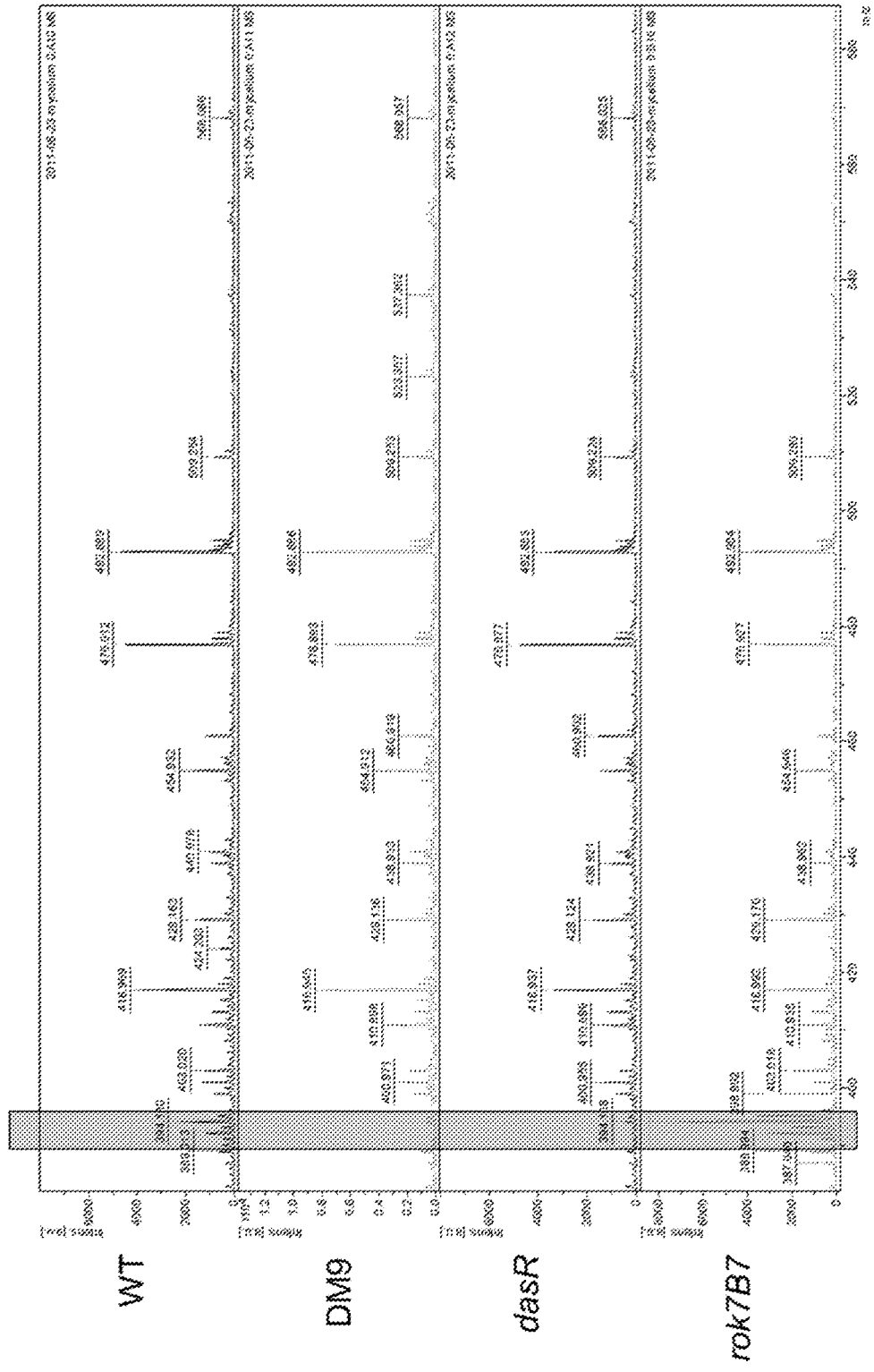
FIG. 3: MALDI-ToF MS analysis of prodiginin production in *S. coelicolor*. Mycelial extracts of *S. coelicolor* parental strain M145 (WT), its deletion mutants dasR and rok7B7, and strain DM9, deficient in prodiginin synthesis, were subject to MALDI-TOF MS analysis. Production of prodoginins could be detected at m/z 392 and 394 as indicated by the shaded area.

To analyze if indeed there was a direct correlation between the expression of the biosynthetic proteins and natural product formation, mycelial (biomass) and spent medium (supernatant) samples obtained from the same cultures as those used for the proteomics samples (Table 1) were analyzed by MALDI-ToF MS. Prodiginin (m/z 392 and 394) was readily detected in mycelial extracts (FIG. 3) and was found to be virtually absent in the dasR null mutant (<10% of wild-type levels) and the DM9 strain which is deficient in prodiginin production. Prodiginin levels were approximately four-fold higher in the rok7B7 mutant, compared to the parental strain. This is in perfect agreement with the proteomics data presented in Table 1, strongly suggesting that indeed protein expression levels can be directly correlated to the amount of secondary metabolite that is produced by the respective biosynthetic clusters.

Figure 4:
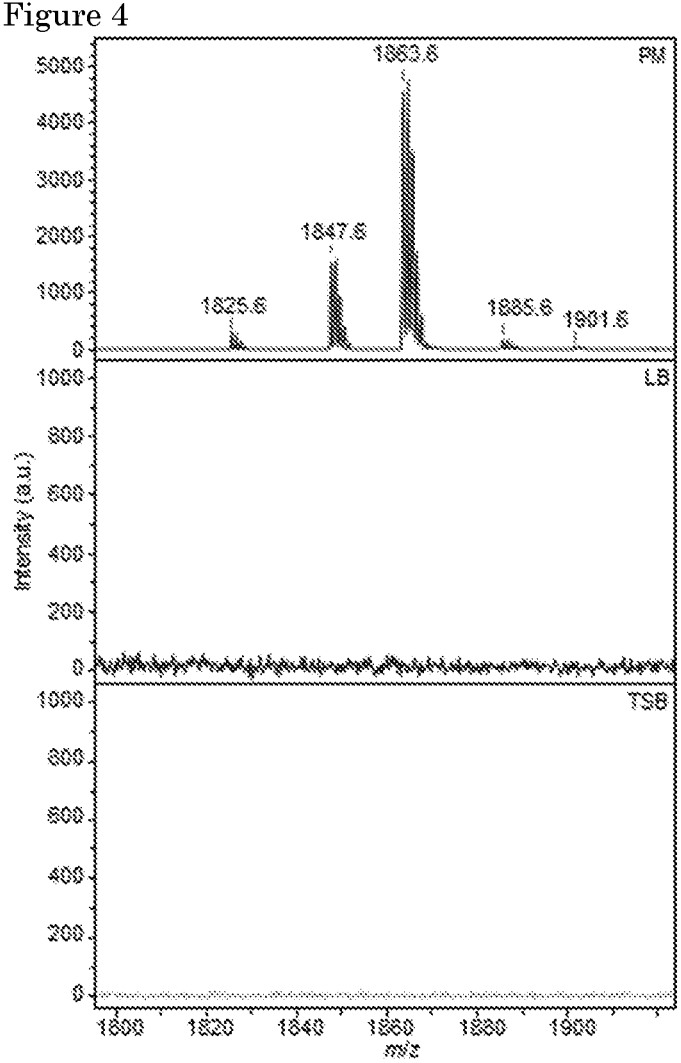
FIG. 4: MALDI-ToF MS analysis of mersacidin production. *B. amyloliquefaciens* HIL-Y85/54728 was grown on indicated media (production medium (PM), Lucia Broth (LB), or trypsinized soy broth (TSB)). a) After five days, spent media samples were subjected to MALDI-ToF MS analysis. Mersacidin production was observed when grown in PM only. The other peaks in the mass range shown corresponded to sodium and potassium adducts of these three isoforms.

We then wondered if this observation could be extended to different types of secondary metabolites and to other microorganisms. Therefore, we analyzed *Bacillus amyloliquefaciens* HIL-Y85/54728 as a second test system, which produces the lantibiotic mersacidin. Lantibiotics are ribosomally encoded peptides that are subsequently modified via among others lanthionine-type thioether crosslinking (Willey & van der Donk, 2007). Mersacidin is a type-B lantibiotic, the synthesis of which is encoded by a gene cluster consisting of ten ORFs (Altena et al., 2000). MALDI-ToF MS analysis of spent medium revealed that it was produced when *B. amyloliquefaciens* was grown in a synthetic production medium but not in the rich media TSB or LB (FIG. 4). Protein extracts were prepared from the same cultures and expression profiles correlated to the levels of mersacidin. Since $^{15}$N metabolic labeling could not be easily performed in this case, dimethyl labeling of peptides (Boersema et al., 2009) was used for quantitative proteomics. Labeled peptides were first fractionated by SCX-HPLC, followed by LC-MS analysis of each fraction. This resulted in the quantification of expression levels of six of the ten mersacidin producing proteins, including the prepeptide MrsA (Table 2). Expression of all proteins was upregulated in the production medium, exemplified by the immunity proteins MrsF and MrsG, and modification protein MrsM (at least twenty-fold upregulated). The cluster-specific regulator MrsR2 was less strongly upregulated (less than two-fold) than the biosynthetic proteins, which is in line with previous observations (van Wezel & McDowall, 2011).

These surprising observations provide important leads for a new and very effective way to connect natural products to its biosynthetic gene cluster. When strains are grown under different growth conditions, production of the secondary metabolite will fluctuate, and along with it the biosynthetic proteins responsible for its production. With the genome sequence known, the proteome can be directly connected to the genome. Therefore, we hypothesized that if a sufficiently large number of different growth conditions is chosen, correlation of expression profiles allows the identification of unique combinations of proteins and metabolites. As an additional constraint, the correlation should preferentially identify multiple biosynthetic proteins encoded by an apparent gene cluster. In this way, proteomics may be used to identify which proteins are responsible and, therefore, which gene cluster belongs to a metabolite of interest, even in a previously uncharacterized organism. We designate this conceptual drug discovery pipeline proteomining.

As a proof of principle, we isolated an uncharacterized *Streptomyces* strain from forest soil that could produce a yellow pigment with strong antimicrobial activity. This strain was designated *Streptomyces* sp. Che1 and was grown in NMMP for 5 days using six different additives to create varying growth conditions: (A) NaOH to pH 9, (B) 25 mM N-acetylglucosamine, (C) 0.8% (w/v) Bacto peptone (Difco), (D) 0.5% (w/v) yeast extract, (E) 2% (w/v) NaCl, (F) 0.5% (w/v) soy flower. Culture supernatants displayed strong variation in the degree of yellow pigmentation, indicative of strong variation in the production of the compound of interest. Each culture supernatant was tested for antibiotic activity against *M. luteus* (FIG. 5a). Supernatants obtained after growth under condition A had highest antimicrobial activity (hallo size of 27.5 mm), conditions C and D resulted in medium sized halos (14.5 mm and 11.5 mm, respectively), while conditions B, E, and F did not induce detectable antimicrobial activity. The antimicrobial activity of the extracts was directly proportional to the degree of yellow pigmentation.

The genome sequence of *Streptomyces* sp. Che1 was obtained using a single run of paired end Illumina sequencing (100 bp reads) and the output was assembled in 919 contigs. Open reading frames were predicted using the genemark algorithm and a database of 8,812 putative (and possibly partial) protein sequences was derived, and served as the reference databases for proteomics. Because only three different labels are available in dimethyl labeling, the samples were compared in two independent quantitative proteomics experiments with one sample in common (A,B,C and A,D,E, respectively), and each experiment containing at least a sample of high activity, and a sample of low activity (FIG. 5b). Protein quantifications of the two experiments were combined, resulting in the identification of 2,645 proteins for Che1, with 1,863 proteins quantified in all comparisons with at least three independent events.

Figure 6:
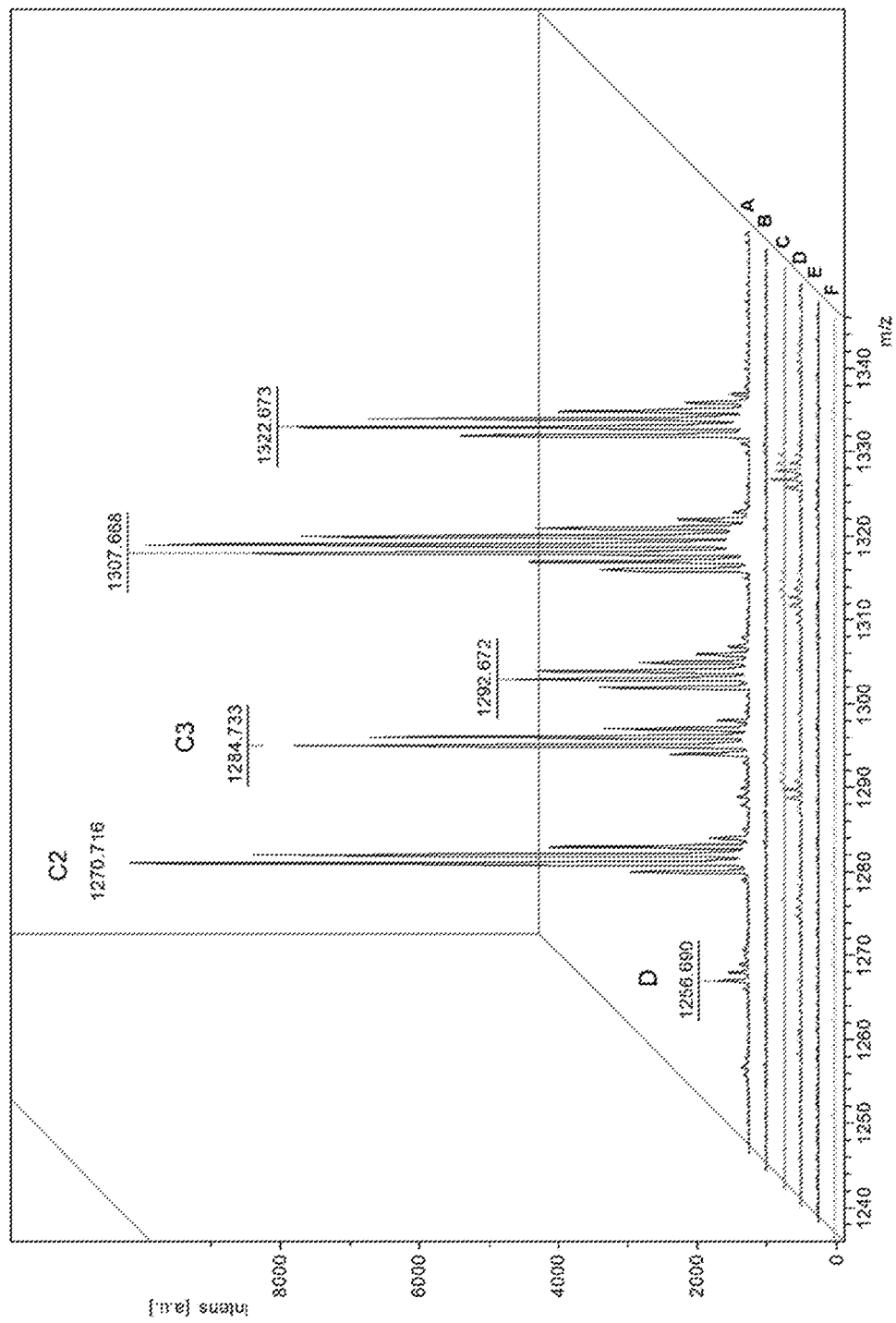
FIG. 6: MALDI-ToF MS analysis of culture supernatants of *Streptomyces* sp. Che1. After growth in conditions A-F as described in the legend of FIG. 5, culture supernatants were subject to MALDI-ToF MS analysis. Three isoforms of actinomycin (D, C2, and C3) could be identified for conditions A, C, and D, as indicated. The other peaks in mass range shown corresponded to sodium and potassium adducts of these three isoforms.

To select proteins of interest, for each comparison, the expression ratios were divided into three similarly sized quantiles: upregulated, downregulated or unchanged. We applied filtering to the four comparisons that included the proteome for the culture grown under condition A, since this culture demonstrated very high activity as compared to the others. In total, seven contigs with at least five matching ORFs clustered together (<10 non-matching or undetected ORFs in between) were selected (Table 3). Closer inspection of these contigs by annotation based on BLAST similarity searches and antiSMASH biosynthesis cluster identification (Medema et al., 2011) suggested that five contained features related to natural product biosynthesis (Table 3), while the other two contained genes for the NADH-dehydrogenase complex. (Keller et al., 2010). In conclusion, proteomining yielded four potential secondary metabolites that correlated to the antimicrobial activity, namely actinomycin (Keller et al., 2010) (Genbank accession HM038106, 48 kb, two contigs), nonactin (Walczak et al., 2000) (Genbank accessions AF263011, 16 kb and AF074603, 16 kb), skyllamycin (Pohle et al., 2011) (Genbank accession JF430460, 87 kb), and an unknown NRPS product, the biosynthetic gene cluster of which was also found in *Streptomyces* species W007 (Genbank accession AGSW0100016). Since several of the candidate natural products were already known, MALDI-ToF MS analysis allowed positive identification of the bioactive compound. Three mono-isotopic masses (1,255 Da, 1,269 Da, and 1,283 Da; FIG. 6) corresponded exactly to the masses expected for actinomycin C2, C3 and D (C1) (Keller et al., 2010), and these were confirmed by proton NMR (data not shown). The additional higher molecular weight peaks were most probably Na+ or K+ adducts of these (+22 Da, and +38 Da, respectively). Signal intensities for all these peaks were strictly coregulated between conditions and demonstrated high correlation to antibiotic activity (high signal for condition A, low signal for conditions C and D, and no detectable signal for the other conditions). This strongly suggested that the observed antimicrobial activity corresponded to actinomycin.

By using the known sequence of the actinomycin cluster as input, we could validate the accuracy of our technology, which was based on a single next generation sequencing run. Additional contigs (237, 414, 925, 793, and 1020, Table 4) were positively mapped to the actinomycin gene cluster by using the Nucmer algorithm (Kurtz et al., 2004), increasing sequence coverage of the cluster to 91%. With one exception, the additional ORFs also matched our filter criteria, but were not identified previously due to the fact that the contigs were too small (less than five ORFs) or, in case of contig 793, contained only a minor section of the actinomycin production cluster. Interestingly, when the threshold value was lowered to three matching ORFs per cluster, contig 237 was the only additional identified contig that clearly coded for biosynthetic activity (not shown). In total, the products of 28 potential ORFs were detected in our experiment (Table 4), 18 of which matched the expected expression pattern. This demonstrates that the assembled contigs obtained from a single run of next generation sequencing (Illumina paired end) provided more than sufficient information for the positive identification of the biosynthetic machinery responsible for actinomycin production.

Figure 7:
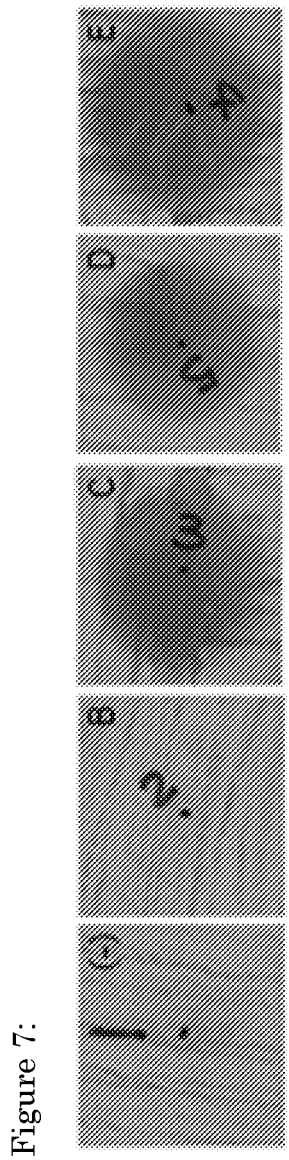
FIG. 7: Proteomining of *Streptomyces* sp. HM151. *Streptomyces* sp. HM151 was grown in liquid NMMP media for 4 days using (−) no additive or with (B) 25 mM N-acetylglucosamine, (C) 0.8% (w/v) Bacto peptone (Difco), (D) 0.5% (w/v) yeast extract, (E) 1% (w/v) NaCl, added respectively. Supernatants were tested for antibiotics production using *M. luteus* as indicator strain.

To further corroborate the applicability of the proteomining concept, we analyzed a second previously undescribed soil isolate, designated *Streptomyces* sp. HM151. Supernatants from cultures grown for four days under conditions C and E contained strong antimicrobial activity, while in cultures grown under condition D had slightly lower activity (FIG. 7). Minute activity was observed when no additive was used (−) and no detectable activity for growth under condition B.

Sequencing of HM151 yielded 396 contigs coding for 8,449 potential protein sequences. Protein expression profiles of cultures grown under conditions (−), C, and E (experiment 1), and B, C, and D (experiment 2) were compared by quantitative proteomics (FIG. 5b), yielding 2,132 protein identifications, with 1,087 proteins quantified in all comparisons. Similar filtering as described for *Streptomyces* sp. Che1 was applied to *Streptomyces* sp. HM151, using the four comparisons of conditions C and E with high antimicrobial activity to the other conditions with reduced or no activity. With three clustered matching hits, the only candidate stretch of the HM151 genome was found in contig 561 between ORFs 118-122 (Table 5). BLAST analysis revealed the candidate cluster to be highly similar (>98%) to a polyketide producing gene cluster in *Streptomyces antibioticus* (Genbank accession Y19177) (Colombo et al., 2001) that codes for the enzymes involved in the first, shared, steps in the synthesis of benzoisochromanequinones, a class of compounds that includes actinorhodin, granaticin, and medermycin (Hopwood, 1997, Ichinose et al., 2003).

Figure 8:
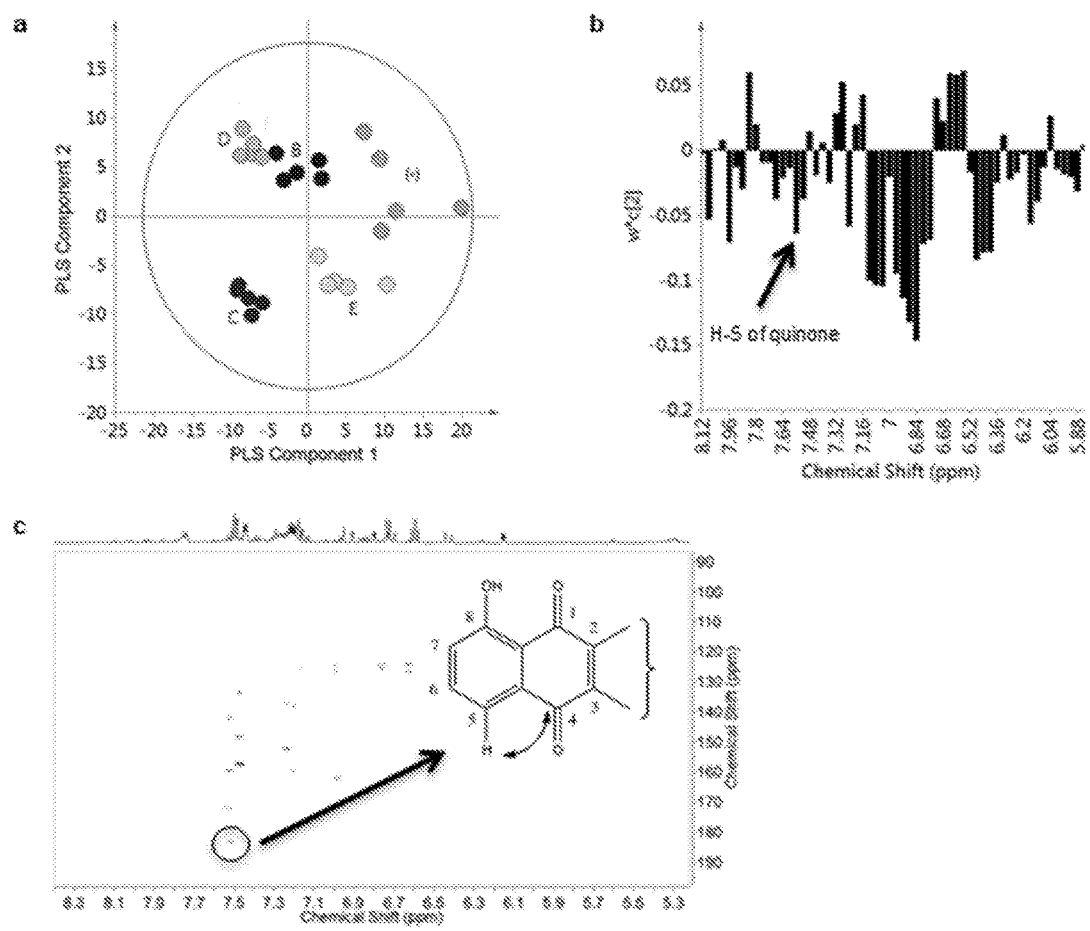
FIG. 8: Metabolomics analysis of *Streptomyces* sp. HM151. Five biological replicates of *Streptomyces* sp. HM151 were grown under the conditions as described for FIG. 7. $^1$H-NMR spectra of EtOAc extracts of spent medium were subjected to partial least square modeling-discriminant analysis (PLS-DA) to obtain a score (a) and loading (b) plot. The ellipse represents the Hotelling T$^2$ with 95% confidence. The arrow indicates the signal obtained for H-5 of naphthoquinone. c) HMBC NMR spectrum of condition C in the range of d 5.2-d 8.4 (horizontal axis for $^1$H) and d 90-d 200 (vertical axis for $^{13}$C). Again, the arrow indicates the signal obtained for H-5 of naphthoquinone.

To link benzoisochromanequinone synthesis under different growth conditions to the observed bioactivity, NMR-based metabolomics (Kim et al., 2010) was applied to EtOAc extracts of spent medium. $^1$H-NMR spectra of five replicates of each condition were analyzed by partial least square modeling-discriminant analysis (PLS-DA, FIGS. 8a and 8b). As shown by the score plot, conditions C and E were found to be quite distinguished from other conditions (FIG. 8a). Main contributors to this difference were several phenolic resonances (FIG. 8b). Particularly, the resonance in δ 7.5-δ 7.6 was identified as an H-5 of naphthoquinone type compounds, which was confirmed by the correlation between H-5 and C4 in a heteronuclear multiple bonds correlation (HMBC) spectrum (FIG. 8c). These data strongly support the synthesis of a medermycin-like compound under conditions C and E, in agreement with our proteomining results.

Figure 9:
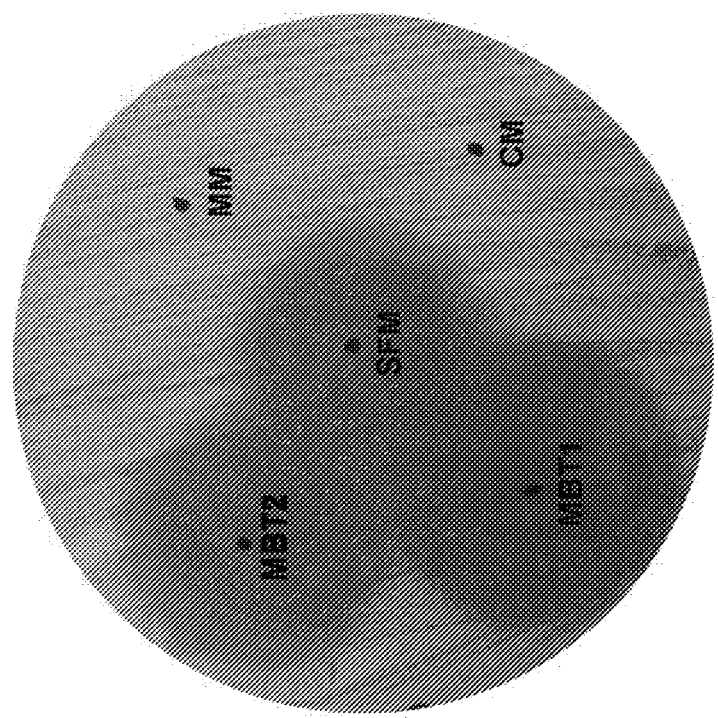
FIG. 9: Proteomining of *Streptomyces* sp. MBT-GE. *Streptomyces* sp. MBT-GE was grown in MM, SFM, MBT1, MBT2 or CM media for 3 days. Supernatants were tested for antibiotic production using *M. luteus* as indicator strain. Antibiotic production is visible as zone of clearing around the supernatant spots.

To further corroborate the applicability of the proteomining concept, we analyzed a third strain designated *Streptomyces* sp. MBT-GE. Best results for this strain were obtained when comparing growth on MM, CM, SFM (all according to Kieser et al., 2000), MBT1 and MBT2 media. MBT1 contains glucose (10 g/l), soy flour (10 g/l) and NaCl (5 g/l) pH 7.5. MBT2 contains soy flour (10 g/l), glucose (25 g/l), peptone (4 g/l), NaCl (2.5 g/l) and CaCO3 (5 g/l), adjusted to pH7.6. Supernatants from cultures grown for three days in MBT1, MBT2 or SFM contained strong antimicrobial activity, while supernatants from cultures grown in MM or CM contained no detectable activity (FIG. 9).

Genome sequencing of MBT-GE yielded 1,585 contigs coding for 8,532 potential protein sequences. Protein expression profiles of cultures grown in MM, MBT1, and MBT2 (experiment 1), and SFM, MBT2, and CM (experiment 2) were compared by quantitative proteomics (FIG. 5b), yielding 2,223 protein identifications, with 1,364 proteins quantified in all comparisons. Again, similar filtering as described for *Streptomyces* sp. Che1 and *Streptomyces* sp. HM151, using the four comparisons between high activity and low activity, was applied. Two candidate contigs were identified containing four and six matching ORFs, respectively. Using BLAST analysis, both contigs were found to be >99% identical to parts of the daunorubicin synthesis cluster of *Streptomyces peucetius*.

In conclusion, the proteomining technology provides a novel concept for the connection of a bioactivity to a gene or gene cluster, using a proteomics approach combined with a (partial) genome sequence. Correlation between bioactivity assays and protein expression profiles under different growth conditions that allow the differential production of the natural product of interest is an efficient way to identify the gene (cluster) responsible for its production. Since this method does not require pre-identification of genes of interest, it should also allow identification of completely new types of natural products, even if the genes have no similarity to any natural product that has been identified so far. We expect that the proteomining technology will facilitate the identification of novel compounds of high medical relevance, such as antibiotics for treatment of the rapidly emerging multidrug resistant pathogens, and anticancer compounds.

TABLE 1

Expression level changes of proteins involved in secondary metabolite synthesis in *S. coelicolor*.

$^2$log ratio (mutant/wt)[a]

| DasR | Rok7B7 | SCO[b] | name[b] | function/pathway[b] |
|---|---|---|---|---|
| 1.7 | 2.0 | SCO0492 | cchH | coelichelin synthesis |
| 1.0 | *1.4* | SCO0494 | cchF | coelichelin synthesis |
| 2.3 | 2.4 | SCO0498 | cchB | coelichelin synthesis |
| 1.7 | 1.9 | SCO0499 | cchA | coelichelin synthesis |
| 2.8 | *1.0* | SCO2782 | DesA | desferrioxamine synthesis |
| 3.0 | 1.9 | SCO2785 | DesD | desferrioxamine synthesis |
| −1.4 | 4.5 | SCO3230 | cdaPS1 | CDA synthesis |
| −1.1 | 4.2 | SCO3231 | cdaPS2 | CDA synthesis |
|  | 4.7 | SCO3232 | cdaPS3 | CDA synthesis |
|  | 3.9 | SCO3236 | asnO | CDA synthesis |
| 3.5 |  | SCO3334 | TrpS1 | Antibiotic resistance |
|  | 1.4 | SCO5878 | redX | prodiginin synthesis |
|  | 1.7 | SCO5879 | redW | prodiginin synthesis |
|  | 1.9 | SCO5888 | fabH3 | prodiginin synthesis |
| −1.8 | 1.9 | SCO5890 |  | prodiginin synthesis |
|  | 2.1 | SCO5891 | redM | prodiginin synthesis |
|  | 2.1 | SCO5892 |  | prodiginin synthesis |
| −2.2 | 1.9 | SCO5895 |  | prodiginin synthesis |
|  | 2.0 | SCO5896 |  | prodiginin synthesis |
| 0.1 | 1.6 | SCO6431 |  | NRPS cluster |
| −0.6 | 2.0 | SCO6436 |  | NRPS cluster |
| 2.6 | *7.8* | SCO6272 |  | cpk cluster |
| 3.1 | *5.6* | SCO6273 | cpkC | cpk cluster |
| 2.8 | *6.6* | SCO6274 | cpkB | cpk cluster |
| 2.9 | *6.1* | SCO6275 | cpkA | cpk cluster |
| 3.3 | *6.2* | SCO6276 |  | cpk cluster |
| 3.5 | *6.2* | SCO6279 |  | cpk cluster |
| 3.5 | 2.8 | SCO6282 |  | cpk cluster |
| 1.5 | 0.9 | SCO7400 | cdtC | siderophore uptake |

[a]protein expression level changes expressed as signal intensity in dasR or rok7B7 deletion mutant vs. signal intensity in parent strain (wt). Data are the average of two experiments, with one experiment using opposite labeling compared to the other experiment (label swap). Italic numbers indicate that the ratio could only be determined in one of the two experiments or demonstrated opposing signs between the two experiments. These numbers are included only if the same protein could be quantified (detected in both experiments with same sign) for the other deletion mutant.
[b]Annotation based on StrepDB located on the World Wide Web at strepdb.streptomyces.org.uk.

TABLE 2

Proteomics analysis of mersacidin production.

| | normalized $^2$log ratios[a] | | |
|---|---|---|---|
| gene | TSB/LB | PM/LB | PM/TSB |
| MrsG | 0.3 | 4.9 | 4.4 |
| MrsR2 | 0.4 | 0.9 | 0.4 |
| MrsF | −0.4 | 5.0 | 5.7 |
| MrsM | −0.1 | 5.1 | 5.6 |
| Mrs T | 1.0 | 3.6 | 2.1 |
| MrsA | 1.6 | 3.4 | 1.3 |

[a]*B. amyloliquefaciens* HIL-Y85/54728 was grown on indicated media (production medium (PM), Lucia Broth (LB), or trypsinized soy broth (TSB)). Protein extracts after one day of growth were subjected to proteomics analysis. All six detected proteins involved in mersacidin production demonstrated elevated levels in production medium.

TABLE 3

Candidate clusters demonstrating expected expression level changes in *Streptomyces* sp. Che1.

| contig[a] | ORFs | ID | Match | first ORF[b] | last ORF | ORFs in cluster | Anti-SMASH[c] | Blast analysis[d] |
|---|---|---|---|---|---|---|---|---|
| 42 | 30 | 9 | 5 | 3 | 8 | 6 | + | *Streptomyces* sp. W007, contig 00173 |
| 412 | 12 | 9 | 6 | 1 | 6 | 6 | | NADH dehydrogenase/complex 1 |
| 419 | 19 | 13 | 6 | 1 | 8 | 8 | | NADH dehydrogenase/complex 1 |
| 814 | 34 | 23 | 17 | 12 | 32 | 21 | + | nonactin |
| 816 | 11 | 8 | 6 | 1 | 8 | 8 | + | actinomycin |
| 981 | 33 | 12 | 5 | 1 | 12 | 12 | + | actinomycin |
| 1256 | 26 | 13 | 8 | 3 | 20 | 18 | + | skyllamycin |

Figure 5:
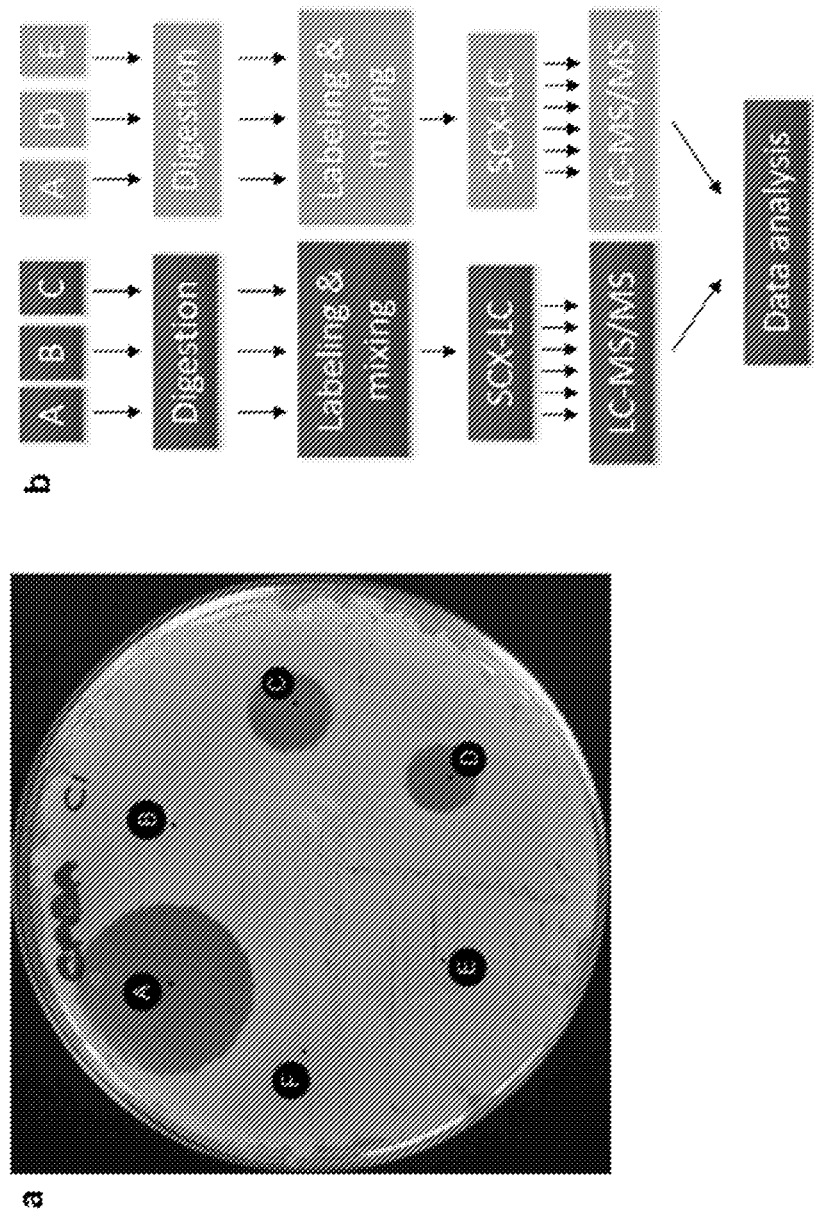
FIG. 5: Proteomining of *Streptomyces* sp. Che1. *Streptomyces* sp. Che1 was grown in liquid NMMP media for 5 days using 6 different additives: (A) NaOH to pH 9, (B) 25 mM N-acetylglucosamine, (C) 0.8% (w/v) Bacto peptone (Difco), (D) 0.5% (w/v) yeast extract, (E) 2% (w/v) NaCl, (F) 0.5% (w/v) soy flower. Supernatants were tested for antibiotics production using *M. luteus* as indicator strain (a). Protein levels in mycelia from five conditions (A-E) were compared using quantitative proteomics (b). Stable istope labeling was performed through dimethylation of tryptic peptides. Since this method allows the comparison of three samples simultaneously, two experiments were performed, using condition A as a shared condition.

[a]Protein expression level changes for the protein products were compared between growth conditions (A-E, see main text and FIG. 5). Expression ratios were divided in three equally sized quantiles for each comparison and filtered based on the four comparisons with the largest change in antibacterial activity (see main text). Contigs with at least 5 matching ORFs in a cluster (max gap <10 ORFs) were selected.
[b]The region between the first matching ORF and last matching ORF was defined as a cluster as to compare the number of matching ORFs to the number of ORFs in the cluster.
[c]Contigs were analyzed with antiSMASH (Medema et al., 2011) for the presence of secondary metabolite biosynthesis clusters. A hit is indicated with '+'.
[d]Sequences were compared using BLAST analysis to known *streptomycetes* sequences in the NCBI nr/nt and WGS (genomic shotgun sequences) databases. Hits with more than 95% identity were used for annotation.

TABLE 4

Expression level changes of ORFs coding for actinomycin biosynthesis.

| contig | ORF | gene[d] | Normalized ratios (2log)[a] | | | | | | Quantiles[b] | | | |
|---|---|---|---|---|---|---|---|---|---|---|---|---|
| | | | B/A | C/A | C/B | D/A | E/A | E/D | B/A | C/A | C/B | D/A |
| 981 | 23 | AcmrC | −2.8 | 0.0 | 2.4 | −3.5 | −3.3 | 0.3 | Q1 | Q2 | Q3 | Q1 |
| 981 | 22 | AcmrB | −3.1 | −0.3 | 2.8 | −2.9 | −2.0 | 1.9 | Q1 | Q2 | Q3 | Q1 |
| 981 | 21 | AcmrA | −3.6 | −0.3 | 3.2 | −4.2 | −3.6 | 0.9 | Q1 | Q2 | Q3 | Q1 |
| 981 | 20 | AcmQ | −2.8 | 0.9 | 3.3 | −3.2 | −1.7 | 1.4 | Q1 | Q3 | Q3 | Q1 |
| 981 | 19 | AcmQ | −2.0 | 1.0 | 2.9 | −3.6 | −2.6 | 0.9 | Q1 | Q3 | Q3 | Q1 |
| 981 | 18 | AcmP | −1.7 | 0.9 | 2.4 | −1.3 | −1.6 | 0.1 | Q1 | Q3 | Q3 | Q2 |
| 981 | 12 | AcmT | −2.8 | −2.2 | 0.4 | −2.1 | −3.8 | −0.8 | Q1 | Q1 | Q3 | Q1 |
| 981 | 11 | AcmS | −2.6 | −2.3 | 0.4 | −3.5 | −3.0 | 0.3 | Q1 | Q1 | Q3 | Q1 |
| 981 | 8 | AcmA | −2.5 | −1.2 | 1.2 | −3.7 | −3.0 | 0.9 | Q1 | Q1 | Q3 | Q1 |
| 981 | 4 | AcmB | −3.6 | −3.1 | 0.5 | −4.0 | −4.7 | −0.4 | Q1 | Q1 | Q3 | Q1 |
| 981 | 1 | AcmC | −2.1 | −1.2 | 0.6 | −4.0 | −4.6 | −1.0 | Q1 | Q1 | Q3 | Q1 |
| 237 | 4 | AcmB/C | −3.1 | −2.6 | 0.6 | −3.9 | −3.1 | 1.0 | Q1 | Q1 | Q3 | Q1 |
| 237 | 6 | AcmB/C | −3.4 | −2.4 | 0.9 | −3.8 | −3.2 | 0.2 | Q1 | Q1 | Q3 | Q1 |
| 237 | 7 | AcmC | −3.0 | −2.4 | 0.4 | −4.3 | −2.5 | 1.9 | Q1 | Q1 | Q3 | Q1 |
| 1020 | 1 | AcmB | −3.7 | −2.5 | 1.0 | −3.4 | −4.0 | 1.1 | Q1 | Q1 | Q3 | Q1 |
| 1020 | 2 | AcmB/C | −3.3 | −2.5 | 0.6 | −3.7 | −2.3 | 0.5 | Q1 | Q1 | Q3 | Q1 |
| 414 | 1 | AcmB/C | −1.4 | −2.0 | −0.7 | −3.6 | −4.0 | 0.0 | Q1 | Q1 | Q1 | Q1 |
| 925 | 1 | AcmB/C | −3.8 | −2.7 | 1.0 | −1.7 | −1.6 | 0.4 | Q1 | Q1 | Q3 | Q1 |
| 816 | 1 | AcmC | −3.5 | −2.4 | 0.8 | −3.7 | −3.9 | 0.4 | Q1 | Q1 | Q3 | Q1 |
| 816 | 2 | AcmC | −2.9 | −1.8 | 1.0 | −3.2 | −3.1 | 0.7 | Q1 | Q1 | Q3 | Q1 |
| 816 | 3 | AcmE | −2.2 | −2.7 | −0.1 | −3.2 | −2.1 | 0.6 | Q1 | Q1 | Q2 | Q1 |
| 816 | 4 | AcmF | −2.8 | −3.5 | −0.5 | −4.9 | −3.0 | 1.8 | Q1 | Q1 | Q1 | Q1 |
| 816 | 7 | AcmH | −2.0 | −2.6 | −0.2 | −2.3 | −2.3 | 0.3 | Q1 | Q1 | Q2 | Q1 |
| 816 | 8 | AcmI | −3.2 | −2.8 | 0.4 | −4.3 | −3.8 | 0.5 | Q1 | Q1 | Q3 | Q1 |
| 816 | 10 | AcmU | −2.7 | 0.9 | 3.4 | | | | Q1 | Q3 | Q3 | |
| 816 | 11 | AcmV | −2.7 | 0.1 | 2.8 | −3.6 | −3.5 | 0.3 | Q1 | Q3 | Q3 | Q1 |
| 793 | 16 | AcmW | −3.8 | −0.3 | 3.2 | −2.6 | −3.4 | −0.7 | Q1 | Q2 | Q3 | Q1 |
| 793 | 14 | AcmY | −1.7 | 0.4 | 1.9 | | | | Q1 | Q3 | Q3 | |

| contig | ORF | gene[d] | Quantiles[b] | | Quantification events[o] | | | | | |
|---|---|---|---|---|---|---|---|---|---|---|
| | | | E/A | E/D | B/A | C/A | C/B | D/A | E/A | E/D |
| 981 | 23 | AcmrC | Q1 | Q3 | 40 | 40 | 40 | 26 | 26 | 26 |
| 981 | 22 | AcmrB | Q1 | Q3 | 7 | 7 | 7 | 9 | 9 | 9 |
| 981 | 21 | AcmrA | Q1 | Q3 | 31 | 31 | 31 | 22 | 22 | 22 |
| 981 | 20 | AcmQ | Q1 | Q3 | 60 | 60 | 60 | 62 | 60 | 60 |
| 981 | 19 | AcmQ | Q1 | Q3 | 16 | 16 | 16 | 9 | 9 | 9 |
| 981 | 18 | AcmP | Q1 | Q2 | 7 | 7 | 7 | 5 | 5 | 5 |
| 981 | 12 | AcmT | Q1 | Q1 | 11 | 11 | 11 | 18 | 16 | 16 |
| 981 | 11 | AcmS | Q1 | Q3 | 52 | 52 | 52 | 61 | 57 | 57 |
| 981 | 8 | AcmA | Q1 | Q3 | 39 | 38 | 38 | 38 | 33 | 33 |
| 981 | 4 | AcmB | Q1 | Q2 | 20 | 20 | 20 | 25 | 23 | 23 |
| 981 | 1 | AcmC | Q1 | Q1 | 15 | 15 | 15 | 9 | 9 | 9 |

TABLE 4-continued

Expression level changes of ORFs coding for actinomycin biosynthesis.

| | | | | | | | | | | |
|---|---|---|---|---|---|---|---|---|---|---|
| 237 | 4 | *AcmB/C* | Q1 | Q3 | 72 | 72 | 72 | 84 | 81 | 81 |
| 237 | 6 | *AcmB/C* | Q1 | Q3 | 44 | 44 | 44 | 43 | 41 | 41 |
| 237 | 7 | *AcmC* | Q1 | Q3 | 12 | 12 | 12 | 15 | 15 | 15 |
| 1020 | 1 | *AcmB* | Q1 | Q3 | 23 | 23 | 23 | 14 | 14 | 14 |
| 1020 | 2 | *AcmB/C* | Q1 | Q3 | 11 | 11 | 11 | 13 | 13 | 13 |
| 414 | 1 | *AcmB/C* | Q1 | Q2 | 3 | 3 | 3 | 3 | 3 | 3 |
| 925 | 1 | *AcmB/C* | Q1 | Q3 | 7 | 7 | 7 | 4 | 4 | 4 |
| 816 | 1 | *AcmC* | Q1 | Q3 | 46 | 46 | 46 | 46 | 38 | 38 |
| 816 | 2 | *AcmC* | Q1 | Q3 | 39 | 39 | 39 | 44 | 42 | 42 |
| 816 | 3 | *AcmE* | Q1 | Q3 | 10 | 10 | 10 | 16 | 15 | 15 |
| 816 | 4 | *AcmF* | Q1 | Q3 | 3 | 3 | 3 | 5 | 5 | 5 |
| 816 | 7 | *AcmH* | Q1 | Q3 | 15 | 15 | 15 | 21 | 20 | 20 |
| 816 | 8 | *AcmI* | Q1 | Q3 | 103 | 100 | 100 | 106 | 99 | 99 |
| 816 | 10 | *AcmU* | | | 4 | 4 | 4 | *2* | *2* | *2* |
| 816 | 11 | *AcmV* | Q1 | Q3 | 40 | 40 | 40 | 32 | 32 | 32 |
| 793 | 16 | *AcmW* | Q1 | Q1 | 14 | 14 | 14 | 10 | 10 | 10 |
| 793 | 14 | *AcmY* | | | 5 | 5 | 5 | *2* | *2* | *2* |

[a]Protein expression level changes observed for the protein products of the indicated ORFs when compared between growth conditions A-E (see main text and FIG. 5).
[b]Expression ratios were divided in three equally sized quantiles for each experiment. In case the expression level change corresponded to the expected quantile this is indicated in bold. In case all four comparisons used for filtering (B/A, C/A, D/A, and E/A) matched to the expected quantile, the ORF number/gene name is also indicated in bold.
[c]Number of quantifications events used to calculate the expression ratios. Quantifications based on less than three events (italicized) were discarded.
[d]Gene name according to GenBank.

TABLE 5

Expression level changes for proteomining hit in contig 561 of *streptomyces* sp. HM151

| | normalized ratios (2log)[a] | | | | | | quantiles[b] | | | | | | quantification events[c] | | | | | |
|---|---|---|---|---|---|---|---|---|---|---|---|---|---|---|---|---|---|---|
| ORF | —/C | E/C | E/— | B/C | D/C | D/B | —/C | E/C | E/— | B/C | D/C | D/B | —/C | E/C | E/— | B/C | D/C | D/B |
| 118 | -0.6 | 1.3 | 1.9 | -2.7 | -3.7 | -0.5 | Q1 | Q3 | Q3 | Q1 | Q1 | Q2 | 21 | 21 | 21 | 7 | 7 | 7 |
| 119 | -0.6 | 1.1 | 1.7 | -3.1 | -5.7 | -1.7 | Q1 | Q3 | Q3 | Q1 | Q1 | Q1 | 16 | 16 | 16 | 4 | 4 | 4 |
| 121 | -1.6 | 0.2 | 2.2 | | | | Q1 | Q2 | Q3 | | | | *5* | *5* | *5* | *2* | *2* | *2* |
| 122 | -0.8 | 0.4 | 1.5 | -3.5 | -5.8 | -1.9 | Q1 | Q2 | Q3 | Q1 | Q1 | Q1 | 31 | 31 | 31 | 13 | 13 | 13 |

[a]Protein expression level changes observed for the protein products of the indicated ORFs when compared between growth conditions B-E (see main text and FIG. 5) and without additive (—).
[b]Expression ratios were divided in three equally sized quantiles for each experiment. In case the expression level change corresponded to the expected quantile this is indicated in bold. In case all four comparisons used for filtering (—/C, E/—, B/C, D/C) matched to the expected quantile, the ORF number is also indicated in bold.
[c]Number of quantifications events used to calculate the expression ratios. Quantifications based on less than three events (italicized) were discarded.

TABLE 6

Expression level changes for proteomining hits of *streptomyces* sp. MBT-GE

| | Normalized Ratios (2log)[a] | | | | | | Quantiles[b] | | | |
|---|---|---|---|---|---|---|---|---|---|---|
| ORF | MBT1/MBT2 | MM/MBT2 | MM/MBT1 | SFM/MBT2 | CM/MBT2 | CM/SFM | MBT1/MBT2 | MM/MBT2 | MM/MBT1 | SFM/MBT2 |
| Contig 626 | | | | | | | | | | |
| 1 | -1.5 | -3.3 | -1.6 | -2.4 | -3.7 | -1.1 | Q1 | Q1 | Q1 | Q1 |
| 2 | 0.9 | -5.7 | -6.7 | -1.9 | -3.9 | -2.0 | Q3 | Q1 | Q1 | Q1 |
| 3 | 0.1 | -2.5 | -2.0 | -2.2 | -3.9 | -1.8 | Q2 | Q1 | Q1 | Q1 |
| 4 | 0.9 | -3.3 | -4.2 | -2.0 | -3.5 | -1.7 | Q3 | Q1 | Q1 | Q1 |
| 5 | 0.8 | -2.0 | -2.7 | | | | Q3 | Q1 | Q1 | |
| Contig 1265 | | | | | | | | | | |
| 1 | 0.6 | -4.4 | -4.6 | -1.4 | -3.1 | -2.7 | Q3 | Q1 | Q1 | Q1 |
| 2 | 0.2 | -3.4 | -3.8 | -1.9 | -2.4 | -0.3 | Q2 | Q1 | Q1 | Q1 |
| 3 | -0.5 | -5.0 | -4.7 | -2.0 | -3.5 | -1.3 | Q2 | Q1 | Q1 | Q1 |
| 4 | 0.7 | -4.3 | -4.8 | -2.2 | -3.7 | -1.7 | Q3 | Q1 | Q1 | Q1 |
| 5 | 0.9 | -3.1 | -3.8 | -1.4 | -3.5 | -1.7 | Q3 | Q1 | Q1 | Q1 |
| 7 | 0.0 | -4.4 | -3.3 | -2.0 | -4.2 | -2.4 | Q2 | Q1 | Q1 | Q1 |

| | Quantiles[b] | | Quantification Events[c] | | | | |
|---|---|---|---|---|---|---|---|
| ORF | CM/MBT2 | CM/SFM | MBT1/MBT2 | MM/MBT2 | MM/MBT1 | SFM/MBT2 | CM/MBT2 | CM/SFM |

TABLE 6-continued

Expression level changes for proteomining hits of *streptomyces* sp. MBT-GE

| | | | | | | | | |
|---|---|---|---|---|---|---|---|---|
| Contig 626 | | | | | | | | |
| 1 | Q1 | Q1 | 4 | 4 | 4 | 7 | 7 | 7 |
| 2 | Q1 | Q1 | 46 | 43 | 43 | 38 | 34 | 34 |
| 3 | Q1 | Q1 | 18 | 16 | 16 | 21 | 21 | 21 |
| 4 | Q1 | Q1 | 13 | 13 | 13 | 8 | 8 | 8 |
| 5 | | | 3 | 3 | 3 | 2 | 2 | 2 |
| Contig 1265 | | | | | | | | |
| 1 | Q1 | Q1 | 31 | 29 | 29 | 41 | 35 | 35 |
| 2 | Q1 | Q1 | 9 | 8 | 8 | 9 | 8 | 8 |
| 3 | Q1 | Q1 | 7 | 4 | 4 | 20 | 19 | 19 |
| 4 | Q1 | Q1 | 53 | 49 | 49 | 51 | 44 | 44 |
| 5 | Q1 | Q1 | 12 | 12 | 12 | 16 | 16 | 16 |
| 7 | Q1 | Q1 | 37 | 35 | 35 | 39 | 39 | 39 |

[a] Protein expression level changes observed for the protein products of the indicated ORFs when compared between growth conditions (see main text and FIG. 9)
[b] Expression ratios were divided in three equally sized quantiles for each experiment. In case the expression level change corresponded to the expected quantile this is indicated in bold. In case all four comparisons used for filtering (-MM/MBT2, MM/MBT1, CM/MBT2, CM/SFM) matched to the expected quantile, the ORF number is also indicated in bold.
[c] Number of quantifications events used to calculate the expression ratios. Quantifications based on less than three events (italicized) were discarded.

REFERENCES

Altena, K., A. Guder, C. Cramer & G. Bierbaum, (2000) Biosynthesis of the lantibiotic mersacidin: organization of a type B lantibiotic gene cluster. *Appl. Environ. Microbiol.* 66: 2565-2571.

Appleyard, A. N., S. Choi, D. M. Read, A. Lightfoot, S. Boakes, A. Hoffmann, I. Chopra, G. Bierbaum, B. A. Rudd, M. J. Dawson & J. Cortes, (2009) Dissecting structural and functional diversity of the lantibiotic mersacidin. *Chem. Biol.* 16: 490-498.

Barona-Gomez, F., S. Lautru, F. X. Francou, P. Leblond, J. L. Pernodet & G. L. Challis, (2006) Multiple biosynthetic and uptake systems mediate siderophore-dependent iron acquisition in *Streptomyces coelicolor* A3(2) and *Streptomyces ambofaciens* ATCC 23877. *Microbiology* 152: 3355-3366.

Bennett, J. W., (1998) Mycotechnology: the role of fungi in biotechnology. *J. Biotechnol.* 66: 101-107.

Boersema, P. J., R. Raijmakers, S. Lemeer, S. Mohammed & A. J. Heck, (2009) Multiplex peptide stable isotope dimethyl labeling for quantitative proteomics. *Nat. Protoc.* 4: 484-494.

Colombo, V., M. Fernandez-de-Heredia & F. Malpartida, (2001) A polyketide biosynthetic gene cluster from *Streptomyces antibioticus* includes a LysR-type transcriptional regulator. *Microbiology* 147: 3083-3092.

Cox, J. & M. Mann, (2008) MaxQuant enables high peptide identification rates, individualized p.p.b.-range mass accuracies and proteome-wide protein quantification. *Nat. Biotechnol.* 26: 1367-1372.

Craig, M., S. Lambert, S. Jourdan, E. Tenconi, S. Colson, M. Maciejewska, M. Ongena, J. F. Martin, G. van Wezel & S. Rigali, (2012) Unsuspected control of siderophore production by N-acetylglucosamine in streptomycetes. *Environ. Microbiol. Rep.* 4: 512-521.

Demain, A. L., (1991) Production of beta-lactam antibiotics and its regulation. *Proc. Natl. Sci. Counc. Repub. China B* 15: 251-265.

Florea, B. I., M. Verdoes, N. Li, W. A. van der Linden, P. P. Geurink, H. van den Elst, T. Hofmann, A. de Ru, P. A. van Veelen, K. Tanaka, K. Sasaki, S. Murata, H. den Dulk, J. Brouwer, F. A. Ossendorp, A. F. Kisselev & H. S. Overkleeft, (2010) Activity-based profiling reveals reactivity of the murine thymoproteasome-specific subunit beta5t. *Chem. Biol.* 17: 795-801.

Gubbens, J., M. Janus, B. I. Florea, H. S. Overkleeft & G. P. van Wezel, (2012) Identification of glucose kinase-dependent and -independent pathways for carbon control of primary metabolism, development and antibiotic production in *Streptomyces coelicolor* by quantitative proteomics. *Mol. Microbiol.* 86: 1490-1507.

Herzner, A. M., J. Dischinger, C. Szekat, M. Josten, S. Schmitz, A. Yakeleba, R. Reinartz, A. Jansen, H. G. Sahl, J. Piel & G. Bierbaum, (2011) Expression of the lantibiotic mersacidin in *Bacillus amyloliquefaciens* FZB42. *PLoS ONE* 6: e22389.

Hopwood, D. A., (1997) Genetic Contributions to Understanding Polyketide Synthases. *Chem. Rev.* 97: 2465-2498.

Hopwood, D. A., K. F. Chater & M. J. Bibb, (1995) Genetics of antibiotic production in *Streptomyces coelicolor* A3(2), a model streptomycete. *Biotechnology* 28: 65-102.

Ichinose, K., M. Ozawa, K. Itou, K. Kunieda & Y. Ebizuka, (2003) Cloning, sequencing and heterologous expression of the medermycin biosynthetic gene cluster of *Streptomyces* sp. AM-7161: towards comparative analysis of the benzoisochromanequinone gene clusters. *Microbiology* 149: 1633-1645.

Keller, U., M. Lang, I. Crnovcic, F. Pfennig & F. Schauwecker, (2010) The actinomycin biosynthetic gene cluster of *Streptomyces* chrysomallus: a genetic hall of mirrors for synthesis of a molecule with mirror symmetry. *J Bacteriol.* 192: 2583-2595.

Kieser, T., M. J. Bibb, M. J. Buttner, K. F. Chater & D. A. Hopwood, (2000) *Practical streptomyces genetics*, p. 613 p. John Innes Foundation, Norwich.

Kim, H. K., Y. H. Choi & R. Verpoorte, (2010) NMR-based metabolomic analysis of plants. *Nat. Protoc.* 5: 536-549.

Kurtz, S., A. Phillippy, A. L. Delcher, M. Smoot, M. Shumway, C. Antonescu & S. L. Salzberg, (2004) Versatile and open software for comparing large genomes. *Genome Biol.* 5: R12.

Lukashin, A. V. & M. Borodovsky, (1998) GeneMark.hmm: new solutions for gene finding. *Nucleic Acids Res.* 26: 1107-1115.

Medema, M. H., K. Blin, P. Cimermancic, V. de Jager, P. Zakrzewski, M. A. Fischbach, T. Weber, E. Takano & R. Breitling, (2011) antiSMASH: rapid identification, annotation and analysis of secondary metabolite biosynthesis gene clusters in bacterial and fungal genome sequences. *Nucleic Acids Res.* 39: W339-346.

Mortensen, P., J. W. Gouw, J. V. Olsen, S. E. Ong, K. T. Rigbolt, J. Bunkenborg, J. Cox, L. J. Foster, A. J. Heck, B. Blagoev, J. S. Andersen & M. Mann, (2010) MSQuant, an open source platform for mass spectrometry-based quantitative proteomics. *J. Proteome Res.* 9: 393-403.

Patel, P., L. Song & G. L. Challis, (2010) Distinct Extracytoplasmic Siderophore Binding Proteins Recognize Ferrioxamines and Ferricoelichelin in *Streptomyces coelicolor* A3(2). *Biochemistry (Mosc.)* 49: 8033-8042.

Pohle, S., C. Appelt, M. Roux, H. P. Fiedler & R. D. Sussmuth, (2011) Biosynthetic gene cluster of the non-ribosomally synthesized cyclodepsipeptide skyllamycin: deciphering unprecedented ways of unusual hydroxylation reactions. *J. Am. Chem. Soc.* 133: 6194-6205.

Rigali, S., H. Nothaft, E. E. Noens, M. Schlicht, S. Colson, M. Muller, B. Joris, H. K. Koerten, D. A. Hopwood, F. Titgemeyer & G. P. van Wezel, (2006) The sugar phosphotransferase system of *Streptomyces coelicolor* is regulated by the GntR-family regulator DasR and links N-acetylglucosamine metabolism to the control of development. *Mol. Microbiol.* 61: 1237-1251.

Rigali, S., F. Titgemeyer, S. Barends, S. Mulder, A. W. Thomae, D. A. Hopwood & G. P. van Wezel, (2008) Feast or famine: the global regulator DasR links nutrient stress to antibiotic production by *Streptomyces*. *EMBO Rep.* 9: 670-675.

Swiatek, M. A., J. Gubbens, G. Bucca, E. Song, Y. H. Yang, E. Laing, B. G. Kim, C. P. Smith & G. P. van Wezel, (2013) The ROK Family Regulator Rok7B7 Pleiotropically Affects Xylose Utilization, Carbon Catabolite Repression, and Antibiotic Production in *Streptomyces coelicolor*. *J. Bacteria* 195: 1236-1248.

van Wezel, G. P. & K. J. McDowall, (2011) The regulation of the secondary metabolism of *Streptomyces*: new links and experimental advances. *Nat. Prod. Rep.* 28: 1311-1333.

Walczak, R. J., A. J. Woo, W. R. Strohl & N. D. Priestley, (2000) Nonactin biosynthesis: the potential nonactin biosynthesis gene cluster contains type II polyketide synthase-like genes. *FEMS Microbiol. Lett.* 183: 171-175.

Willey, J. M. & W. A. van der Donk, (2007) Lantibiotics: peptides of diverse structure and function. *Annu. Rev. Microbiol.* 61: 477-501.

Zerbino, D. R. & E. Birney, (2008) Velvet: algorithms for de novo short read assembly using de Bruijn graphs. *Genome Res.* 18: 821-829.

The invention claimed is:

1. A method for identifying a candidate protein, or a DNA encoding the candidate protein, said method comprising
   culturing said micro-organism under at least two different culture conditions,
   selecting from said different culture conditions at least two cultures in which the level of a product that is produced by said micro-organism is different than the other culture,
   preparing a protein and/or RNA sample from the selected cultures of micro-organisms,
   determining a sequence of at least part of the proteins and/or RNA in said samples,
   selecting sequences of proteins and/or sequences of RNA of which the amount differs between the samples of the selected cultures of micro-organisms,
   grouping selected sequences of proteins and/or sequences of RNA coded for by DNAs into a first group that comprises selected sequences that are separated by no more than 30 open reading frames (ORFs) on the genome of the micro-organism,
   grouping remaining selected sequences of proteins and/or sequences of RNA coded for by DNAs (if any) into a second group that comprises selected sequences that are separated by no more than 30 ORFs on the genome of the micro-organism group,
   identifying a group of selected sequences that contains the coding regions of at least two different RNAs or proteins of which the amount correlates with the level of the product that is produced by said micro-organism under said at least two different culture conditions, and
   identifying a protein or DNA that comprises a sequence of the identified group thereby identifying a candidate protein that is likely involved in the production of the product by said micro-organism.

2. A method according to claim 1, wherein said product is a metabolite or an enzyme.

3. A method according to claim 2, wherein said metabolite is a secondary metabolite.

4. The method according to claim 3, wherein said secondary metabolite is an antibiotic, an antibiotic resistance inhibitor, an anti-cancer compound, an enzyme-inhibitor, an antifungal, an antihelminthic, an immunostimulant, an immunosuppressant, an insecticide, or an herbicide.

5. The method according to claim 3, wherein the identity of the secondary metabolite is not known prior to preparing said samples.

6. The method according to claim 5, further comprising: identifying the secondary metabolite.

7. The method according to claim 1, wherein at least three cultures are selected in which the level of the product that is produced by the micro-organism is different in the different culture conditions.

8. The method according to claim 1, wherein said micro-organism belongs to the phylum *Actinobacteria*.

9. The method according to claim 1, wherein said culture conditions differ from each other in that
   the culture medium has a different pH at the start of the culture,
   the culture conditions differ in the presence, amount and/or type of soil in the culture,
   the culture conditions differ in the presence, amount and/or type of bacterial remains at the start of the culture,
   the culture conditions differ in amount or type of carbon source in the culture medium,
   the culture conditions differ in the amount or type of nitrogen source in the culture medium,
   the culture conditions differ in metal composition,
   the culture conditions differ in the presence, amount and/or type of a further micro-organism in the culture,
   the culture conditions differ in the temperature, and/or
   the culture conditions differ in the presence of a signal molecule.

10. The method according to claim 1, further comprising sequencing at least 50% of the genome of said micro-organism.

11. The method according to claim 1, further comprising isolating the identified gene from the genome of said micro-organism.

12. The method according to claim 11, further comprising: providing a micro-organism of a different species with said identified gene.

13. A method according to claim 12, comprising providing said micro-organism of a different species with the genes of a gene cluster comprising said identified gene.

14. The method according to claim 1, further comprising culturing said micro-organism or said micro-organism of a different species comprising the genes of a gene cluster comprising said identified gene.

15. A method for obtaining a product produced by a micro-organism, said method comprising:
performing the method according to claim 3, and
producing said secondary metabolite by said micro-organism or a micro-organism of a different species comprising the genes of a gene cluster comprising said identified gene and obtaining the produced product.

16. A method for identifying a protein, or a DNA encoding said protein, the method comprising:
culturing a microorganism under at least two different culture conditions,
selecting from the different cultures at least three cultures in which the production level of a product produced by the microorganism is different than the other,
preparing a protein sample and/or RNA sample from each of the at least three selected cultures of microorganisms,
sequencing at least part of the proteins and/or RNA in the samples,
selecting sequences of proteins and/or sequences of RNA of which the amount differs between the samples of the selected cultures of microorganisms,
grouping selected sequences of proteins and/or sequences of RNA encoded by DNAs into a first group comprising selected sequences separated by no more than thirty open reading frames (ORFs) on the microorganism's genome,
grouping any remaining selected sequences of proteins and/or sequences of RNA encoded by DNAs into a second group comprising the selected sequences separated by no more than thirty ORFs on the microorganism's genome, and
identifying a group of the selected sequences that contains the coding regions of at least two different RNAs or proteins of which the amount correlates with the production level of the product.

17. The method according to claim 16, wherein the product is a metabolite, enzyme, or secondary metabolite.

18. The method according to claim 16, wherein the product is an antibiotic, an antibiotic resistance inhibitor, an anti-cancer compound, an enzyme-inhibitor, an antifungal, an antihelminthic, an immunostimulant, an immunosuppressant, an insecticide, or an herbicide.

19. The method according to claim 16, wherein the microorganism belongs to the phylum *Actinobacteria*.

20. The method according to claim 19, wherein the microorganism is a *Streptomyces* bacterium.

* * * * *